US012770348B2

(12) United States Patent
Ni et al.

(10) Patent No.: US 12,770,348 B2
(45) Date of Patent: Oct. 20, 2026

(54) METHODS AND SYSTEMS FOR PROCESSING THREE-DIMENSIONAL MEDICAL IMAGES BASED ON USER'S POSTURES

(71) Applicant: SHANGHAI UNITED IMAGING HEALTHCARE CO., LTD., Shanghai (CN)

(72) Inventors: Cheng Ni, Shanghai (CN); Chengcheng Rong, Shanghai (CN); Jingyi Wu, Shanghai (CN); Wei Zhang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 201 days.

(21) Appl. No.: 18/190,079

(22) Filed: Mar. 25, 2023

(65) Prior Publication Data

US 2023/0306702 A1 Sep. 28, 2023

(30) Foreign Application Priority Data

Mar. 25, 2022 (CN) ......................... 202210301893.8

(51) Int. Cl.
*G06T 19/20* (2011.01)
*G06T 17/00* (2006.01)
(Continued)

(52) U.S. Cl.
CPC .............. *G06T 19/20* (2013.01); *G06T 17/00* (2013.01); *G16H 20/40* (2018.01); *G16H 30/40* (2018.01);
(Continued)

(58) Field of Classification Search
CPC ..... G06T 19/20; G06T 17/00; G06T 2210/41; G06T 2219/2021; G06T 19/00;
(Continued)

(56) References Cited

U.S. PATENT DOCUMENTS 10,043,279 B1 * 8/2018 Eshet ........................ G06T 7/11
10,803,608 B1 * 10/2020 Na ......................... A61B 90/36
(Continued)

FOREIGN PATENT DOCUMENTS

CN 107341791 A 11/2017
CN 107452074 A 12/2017
(Continued)

*Primary Examiner* — Jin Cheng Wang

(74) *Attorney, Agent, or Firm* — METIS IP LLC

(57) ABSTRACT

This present disclosure provides methods and systems processing a three-dimensional image. The method may include: generating a three-dimensional medical image of a target object based on medical imaging data of the target object, and displaying the three-dimensional medical image in a three-dimensional space; obtaining one or more processing instructions of a user; and generating a target medical model by contouring, in the three-dimensional space, based on the one or more processing instructions, the three-dimensional medical image. The three-dimensional medical image may be generated based on medical imaging data of the target object. The target medical model may include three-dimensional contour information.

19 Claims, 12 Drawing Sheets

(51) Int. Cl.
*G16H 20/40* (2018.01)
*G16H 30/40* (2018.01)

(52) U.S. Cl.
CPC .. *G06T 2210/41* (2013.01); *G06T 2219/2021* (2013.01)

(58) Field of Classification Search
CPC ....... G06T 2219/008; G06T 2219/2004; G06T 3/4007; G16H 20/40; G16H 30/40; G16H 30/20; G16H 50/20; G16H 50/50; G16H 50/70; G16H 40/60
See application file for complete search history.

(56) References Cited

U.S. PATENT DOCUMENTS

| | | | | |
|---|---|---|---|---|
| 2006/0064396 | A1* | 3/2006 | Wei | A61B 6/463 |
| 2007/0003016 | A1* | 1/2007 | Brunner | A61B 6/463 378/98.12 |
| 2008/0130825 | A1* | 6/2008 | Fu | G06T 7/248 378/8 |
| 2012/0032953 | A1* | 2/2012 | Schulz | G06T 7/12 345/419 |
| 2017/0071492 | A1* | 3/2017 | van Dam | A61B 5/282 |
| 2019/0252061 | A1* | 8/2019 | Chang | G16H 50/20 |
| 2019/0365350 | A1* | 12/2019 | Chiang | A61B 8/12 |
| 2020/0085382 | A1* | 3/2020 | Taerum | G06T 7/0016 |
| 2020/0105070 | A1* | 4/2020 | Coustaud | G06T 11/60 |
| 2020/0111207 | A1* | 4/2020 | Peng | A61B 6/463 |
| 2020/0273227 | A1* | 8/2020 | Miyaki | A61B 8/461 |
| 2020/0281662 | A1* | 9/2020 | Cong | A61B 8/481 |
| 2020/0380675 | A1* | 12/2020 | Golden | G06T 7/143 |
| 2021/0204914 | A1* | 7/2021 | Meral | G16H 40/63 |
| 2021/0233240 | A1* | 7/2021 | Yan | A61B 6/032 |
| 2021/0233252 | A1* | 7/2021 | Paul | G06T 7/30 |
| 2021/0233330 | A1* | 7/2021 | Sutherland | G06F 3/011 |
| 2021/0327563 | A1* | 10/2021 | He | G06N 3/0464 |
| 2022/0088410 | A1* | 3/2022 | Hibbard | A61N 5/1038 |
| 2022/0108540 | A1* | 4/2022 | Lamash | G06T 19/20 |
| 2022/0160430 | A1* | 5/2022 | Landon | A61B 90/36 |
| 2022/0207645 | A1* | 6/2022 | Kansara | H04N 7/0122 |
| 2022/0305291 | A1* | 9/2022 | Hibbard | A61N 5/1039 |
| 2022/0370033 | A1* | 11/2022 | Klingensmith | A61B 34/10 |
| 2023/0082049 | A1* | 3/2023 | Moreau | G06T 7/12 345/419 |
| 2023/0222748 | A1* | 7/2023 | El Beheiry | G06T 7/62 |
| 2023/0240756 | A1* | 8/2023 | Wiegel | A61B 6/5247 600/424 |
| 2023/0290480 | A1* | 9/2023 | Bose | A61N 5/1039 |
| 2023/0306601 | A1* | 9/2023 | Ruskó | G06T 7/12 |
| 2023/0351586 | A1* | 11/2023 | Brynolfsson | G06T 7/11 |
| 2023/0397816 | A1* | 12/2023 | Forneris | G06T 19/20 |
| 2023/0410301 | A1* | 12/2023 | Rajagopal | G06T 7/12 |

FOREIGN PATENT DOCUMENTS

| | | | |
|---|---|---|---|
| CN | 109785306 | A | 5/2019 |
| CN | 110675464 | A | 1/2020 |
| CN | 111639531 | A | 9/2020 |
| CN | 113362452 | A | 9/2021 |
| CN | 113808111 | A | 12/2021 |

* cited by examiner

METHODS AND SYSTEMS FOR PROCESSING THREE-DIMENSIONAL MEDICAL IMAGES BASED ON USER'S POSTURES

CROSS-REFERENCE TO RELATED APPLICATIONS

This application claims priority of Chinese Patent Application No. 202210301893.8, filed on Mar. 25, 2022, the contents of which are hereby incorporated by reference to its entirety.

TECHNICAL FIELD

The present disclosure relates to the field of medical image processing, and in particular to methods and systems for processing three-dimensional images.

BACKGROUND

Three-dimensional modeling of organs and tumors of an object is important in the radiotherapy planning process. A radiotherapist generally needs to mark a spatial boundary between a target area and a normal organ in a CT, or MR, etc., image of the object for the subsequent physical simulation process.

A common modeling approach is performed based on a two-dimensional (2D) tomographic image of the object, and contours of the target area(s) and/or organ(s) are generated based on grayscale information of the image by using tools such as a brush, an eraser, etc. By contouring 2D images layer by layer, a closed three-dimensional (3D) surface can be reconstructed in 3D space based on the generated 2D contours, and is used as a 3D model representation of the target area(s) and/or organ(s). The above operations are performed based on a traditional 2D working mode, in which a monitor, a mouse, etc., is used to realize the editing and contouring of a 3D model. In comparison with intuitive and convenient 3D operation modes, in the 2D working mode, the technicians concerned (e.g., radiotherapists) need to use the mouse for frequent rotation operations if they change the viewpoint, and edit and modify the contour layer by layer when modifying local areas of the model, which is time-consuming and laborious.

Therefore, it is desired to provide methods and systems for processing three-dimensional images, to facilitate a radiotherapist directly browse and modify contour(s) in a three-dimensional space based on operations consistent with human habits, thereby improving the convenience, operational efficiency, and operational accuracy of contouring.

SUMMARY

One aspect of the present disclosure provides a method implemented on at least one machine each of which has at least one processor and at least one storage device for image processing, and the method comprises: generating a three-dimensional medical image of a target object based on medical imaging data of the target object, and displaying the three-dimensional medical image in a three-dimensional space; obtaining one or more processing instructions of a user; and generating a target medical model by contouring, in the three-dimensional space, based on the one or more processing instructions, the three-dimensional medical image, the target medical model including three-dimensional contour information.

Another aspect of the present disclosure provides a system for processing a three-dimensional image, the system comprises: at least one storage device storing a set of instructions; and at least one processor in communication with the storage device, wherein when executing the set of instructions, the at least one processor is configured to cause the system to perform operations including: generating a three-dimensional medical image of a target object based on medical imaging data of the target object, and displaying the three-dimensional medical image in a three-dimensional space; obtaining one or more processing instructions of a user; and generating a target medical model by contouring, in the three-dimensional space, based on the one or more processing instructions, the three-dimensional medical image, the target medical model including three-dimensional contour information.

A further aspect of the present disclosure provides a non-transitory computer readable medium storing instructions, the instructions, when executed by at least one processor, causing the at least one processor to implement a method comprising: generating a three-dimensional medical image of a target object based on medical imaging data of the target object, and displaying the three-dimensional medical image in a three-dimensional space; obtaining one or more processing instructions of a user; and generating a target medical model by contouring, in the three-dimensional space, based on the one or more processing instructions, the three-dimensional medical image, the target medical model including three-dimensional contour information.

BRIEF DESCRIPTION OF THE DRAWINGS

The present disclosure is further illustrated in terms of exemplary embodiments. These exemplary embodiments are described in detail with reference to the drawings. These embodiments are not limited. In these embodiments, the same number represents the same structure, wherein.

DETAILED DESCRIPTION

Figure 1:
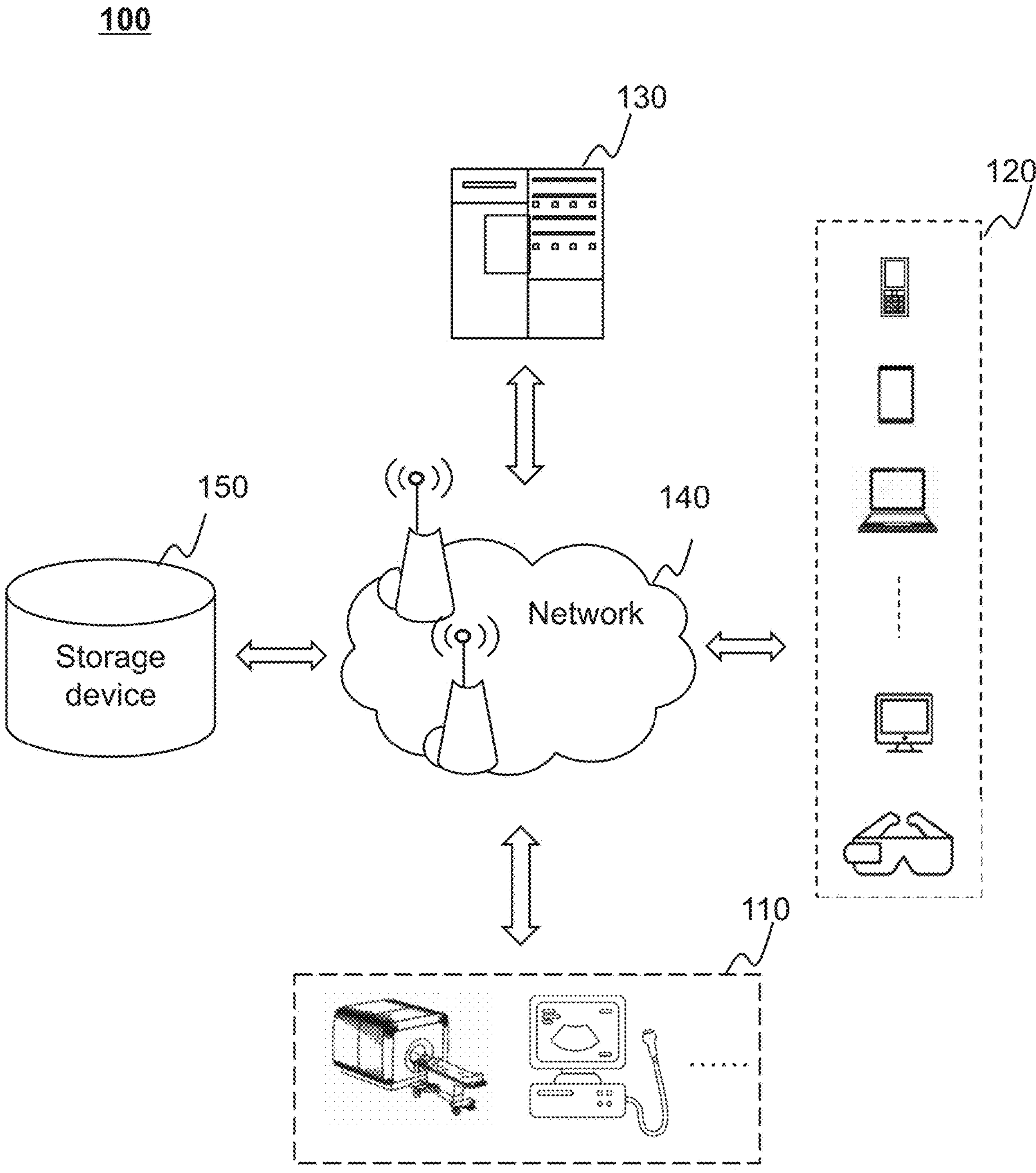
FIG. 1 is a schematic diagram illustrating an application scenario of a system for processing a three-dimensional image according to some embodiments of the present disclosure.

The technical schemes of embodiments of the present disclosure will be more clearly described below, and the accompanying drawings need to be configured in the description of the embodiments will be briefly described below. Obviously, the drawings in the following description are merely some examples or embodiments of the present disclosure, and will be applied to other similar scenarios according to these accompanying drawings without paying creative labor. Unless obviously obtained from the context or the context illustrates otherwise, the same numeral in the drawings refers to the same structure or operation.

It should be understood that the "system", "device", "unit" and/or "module" used herein is a method for distinguishing different components, elements, components, parts or assemblies of different levels. However, if other words may achieve the same purpose, the words may be replaced by other expressions.

As shown in the present disclosure and claims, unless the context clearly prompts the exception, "a", "one", and/or "the" is not specifically singular, and the plural may be included. It will be further understood that the terms "comprise," "comprises," and/or "comprising," "include," "includes," and/or "including," when used in present disclosure, specify the presence of stated features, integers, steps, operations, elements, and/or components, but do not preclude the presence or addition of one or more other features, integers, steps, operations, elements, components, and/or groups thereof.

The flowcharts are used in present disclosure to illustrate the operations performed by the system according to the embodiment of the present disclosure. It should be understood that the preceding or following operations is not necessarily performed in order to accurately. Instead, the operations may be processed in reverse order or simultaneously. Moreover, one or more other operations may be added to the flowcharts. One or more operations may be removed from the flowcharts.

FIG. 1 is a schematic diagram illustrating an application scenario of a system for processing a three-dimensional image according to some embodiments of the present disclosure. As shown in FIG. 1, the system 100 for processing a three-dimensional image may include a medical imaging device 110, a terminal device 120, a processing device 130, a network 140, and a storage device 150.

In some embodiments, the system 100 may process a three-dimensional image by implementing the methods and/or processes disclosed in the present disclosure.

In some embodiments, the medical imaging device 110 may be used to obtain medical imaging data of a target object. In some embodiments, the medical imaging device 110 may be a non-invasive biomedical imaging device for disease diagnosis or research purposes. For example, the medical imaging device may include a single-modality scanner and/or a multi-modality scanner. The single-modality scanner may include, for example, a magnetic resonance imaging (MRI) scanner, a computed tomography (CT) scanner, a positron emission tomography (PET) scanner, a single photon emission computed tomography (SPECT) scanner, an ultrasound examiner, an ultrasound scanner, an X-ray scanner, an optical coherence tomography (OCT) scanner, an ultrasound (US) scanner, an intravascular ultrasound (IVUS) scanner, a near infrared spectroscopy (NIRS) scanner, a far infrared (FIR) scanner, or any combination thereof. The multi-modality scanner may include, for example, a magnetic resonance imaging-single photon emission computed tomography (MRI-SPECT) scanner, a magnetic resonance imaging-x-ray imaging (MRI-X-ray) scanner, a magnetic resonance imaging-digital subtraction angiography (MRI-DSA) scanner, a positron emission tomography-computed tomography (PET-CT) scanner, a positron emission tomography-x-ray imaging (PET-X-ray) scanner, etc. The scanners provided above are for illustrative purposes only and are not intended to limit the scope of the present disclosure. As used herein, the term "imaging modality" or "modality" refers broadly to an imaging method or technique for collecting, generating, processing, and/or analyzing imaging information of a target object.

In some embodiments, the medical imaging device 110 may be used to obtain a three-dimensional medical image of a target object. In some embodiments, the medical imaging device 110 may send the obtained medical imaging data to the processing device 130 for processing to generate a three-dimensional medical image. For more information about the medical imaging data, and the three-dimensional medical image, please refer to FIG. 3 and related descriptions thereof.

The terminal device 120 refers to one or more terminal devices or software used by a user. In some embodiments, the terminal device 120 may be one of a mobile device, a tablet, a laptop, a desktop computer, or other device with input and/or output capabilities, or any combination thereof. In some embodiments, the terminal device 120 may include an augmented reality (AR) device, a virtual reality (VR) device, etc. In some embodiments, the terminal device 120 may be used to display a three-dimensional medical image of a target object and/or a medical model of the target object. For example, the AR device may be used to display the three-dimensional medical image of the target object and/or the target medical model in a real three-dimensional space (i.e., the real world). As another example, software on the laptop, the desktop computer, etc., may be used to display the three-dimensional medical image of the target object and/or the target medical model in a virtual three-dimensional space. In some embodiments, the user may generate the target medical model by contouring the three-dimensional medical image of the target object via the terminal device 120.

In some embodiments, the terminal device 120 may interact with other components in the system 100 for processing a three-dimensional image via the network 140. For example, the terminal device 120 may send one or more control instructions to the processing device 130 to control the processing device 130 to contour the three-dimensional medical image of the target object. In some embodiments, the terminal device 120 may be part of the processing device 130. In some embodiments, the terminal device 120 may be integrated with the processing device 130 as an operator console for the medical imaging device 110.

The processing device 130 may process data and/or information obtained from the medical imaging device 110, the terminal device 120, and/or the storage device 150. The processing device 130 may access the information and/or data via the network 140 or directly from the medical imaging device 110, the terminal device 120, and/or the storage device 150. The processing device 130 may process the obtained data and/or information. For example, the processing device 130 may generate the three-dimensional medical image based on the medical imaging data of the target object. As another example, the processing device 130 may generate a three-dimensional medical model of the target based on a processing instruction of the user to contour the three-dimensional medical image.

In some embodiments, the processing device 130 may process the three-dimensional medical image or an initial medical model of the target object (e.g., model contouring, etc.) and/or perform a medical operation, such as a radiotherapy treatment, a surgical procedure, etc., based on the processed target medical model. In some embodiments, the processing device 130 may be integrated in an electronic device (e.g., a medical device such as an imaging device, a radiotherapy device, etc.), may be an independent electronic device, or may be set in a cloud-based server (e.g., Online Server). For example, the processing device may be a center console of the medical device described above, a personal computer, a laptop computer, a smartphone, a tablet computer, and a portable wearable device, etc.

The network 140 may include any suitable network that is capable of facilitating information and/or data exchange of the system 100 for processing a three-dimensional image. In some embodiments, one or more components of the system 100 for processing a three-dimensional image (e.g., the medical imaging device 110, the terminal device 120, the processing device 130, and the storage device 150) may exchange information and/or data with each other over the network 140. The network 140 may include a local area network (LAN), a wide area network (WAN), a wired network, a wireless network, etc., or any combination thereof.

The storage device 150 may be used to store data, instructions, and/or any other information. In some embodiments, the storage device 150 may store data and/or information obtained from, for example, the medical imaging device 110, the terminal device 120, the processing device 130, or the like. For example, the storage device 150 may store the three-dimensional medical image of the target object, etc. As another example, the storage device 150 may store the processing instruction of the user, etc. The storage device 150 may be provided in the medical imaging device 110. In some embodiments, the storage device 150 may include a mass memory, a removable memory, a volatile read-write memory, a read-only memory (ROM), etc., or any combination thereof. In some embodiments, the storage device 150 may be implemented on a cloud platform.

Figure 2:
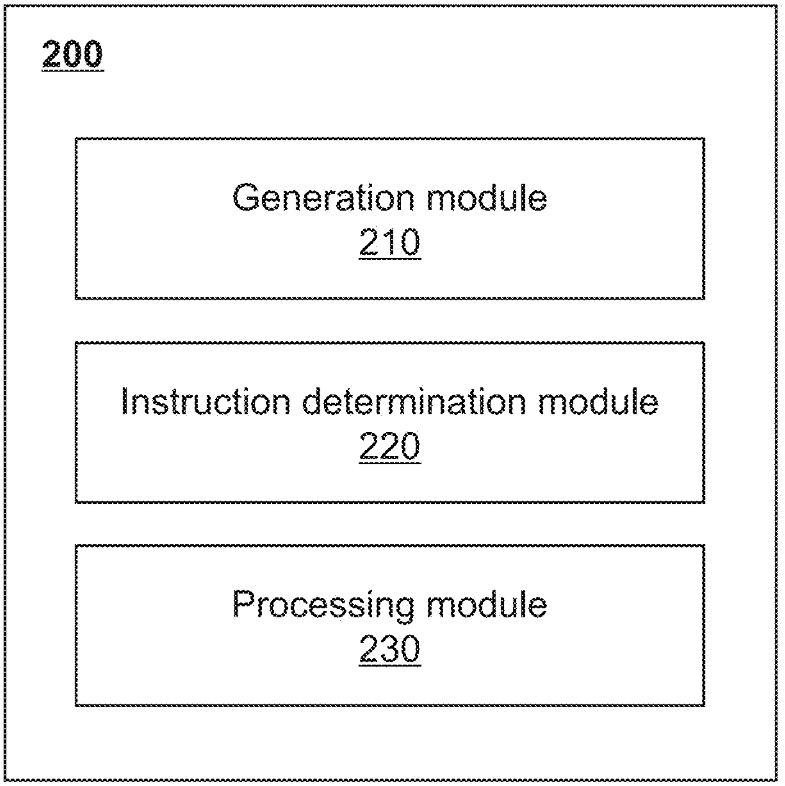
FIG. 2 is a block diagram illustrating an exemplary system for processing a three-dimensional image according to some embodiments of the present disclosure.

FIG. 2 is a block diagram illustrating an exemplary system for processing a three-dimensional image according to some embodiments of the present disclosure.

As shown in FIG. 2, the system 200 for processing a three-dimensional image may include a generation module 210, an instruction determination module 220, and a processing module 230. In some embodiments, the system 200 may be implemented by the processing device 120.

The generation module 210 may be used to display a three-dimensional medical image of a target object in a three-dimensional space.

In some embodiments, the generation module 210 may determine a display parameter of at least one tissue in the three-dimensional medical image based on a tissue type and/or a spatial position relationship between different tissues in medical imaging data. For more information about the display parameter, please refer to FIG. 3 and related descriptions thereof.

In some embodiments, the generation module 210 may determine a second datum plane based on the medical imaging data; generate, based on the medical imaging data and the second datum plane, a two-dimensional rendered image of the target object; and/or display the two-dimensional rendered image in the three-dimensional space. For more information about the two-dimensional rendered image, please refer to FIG. 5 and related descriptions thereof.

In some embodiments, the three-dimensional medical image includes a three-dimensional rendered image, and the generation module 210 may generate the three-dimensional rendered image based on the medical imaging data. For more information about the three-dimensional rendered image, please refer to FIG. 3 and related descriptions thereof.

In some embodiments, the three-dimensional medical image includes an initial medical model of the target object, and the generation module 210 may obtain the initial medical image. For more information about the obtaining the initial medical image, please refer to step 610 and related descriptions thereof.

The instruction determination module 220 may obtain one or more processing instructions of the user.

In some embodiments, the instruction determination module 220 may obtain a user posture, identify the user posture to determine one or more processing instructions corresponding to the user posture.

In some embodiments, the instruction determination module 220 may obtain limb depth information corresponding to the user posture based on a posture identification device; and determine the user posture based on the limb depth information.

The instruction determination module 220 may determine, based on an identification result of the user posture, a target posture operation; and determine, based on a correspondence between posture operations and processing instructions, a processing instruction corresponding to the target posture operation. For more information about the user posture and the determining the processing instruction(s), please refer to FIG. 3, FIG. 10 and their related descriptions.

The processing module 230 may be used to generate a target medical model by contouring the three-dimensional medical image in the three-dimensional space based on the processing instruction(s).

In some embodiments, the target medical model further includes two-dimensional contour information, and the processing module 230 may be used to determine a first datum plane in the three-dimensional medical image; generate the two-dimensional contour information in the first datum plane based on the processing instruction(s). For more information about the two-dimensional contour information, please refer to FIG. 4 and its related description.

In some embodiments, the three-dimensional medical image includes an initial medical model of the target object, and the processing module 230 may generate the target medical model by processing the initial medical model in the three-dimensional space based on the processing instruction(s). For more information about the processing the initial medical model, please refer to FIG. 6 and its related description.

In some embodiments, to obtain the initial medical model, the processing module 230 may determine, based on the medical imaging data, a target region; generate the initial medical model based on a preset processing range and the target region. For more information about the generating the initial medical model based on the preset processing range and target region, please refer to FIG. 6 and its related description.

In some embodiments, to obtain the initial medical model, the processing module 230 may determine three-dimensional boundary information of the target object by processing the medical imaging data based on a first algorithm; and determine the initial medical model based on the three-dimensional boundary information and the medical imaging data. For more information about the determining the initial medical model based on the three-dimensional boundary information, please refer to FIG. 7 and its related description.

In some embodiments, the processing module 230 may generate, in response to a user posture, an operation identification in the three-dimensional space; and process the initial medical model, based on the processing instruction, by the operation identification. For more information about the processing the initial medical model by the operation identification, please refer to FIG. 8, FIG. 9 and their related descriptions.

It should be noted that the above description of the system 200 for processing a three-dimensional image and its modules is for descriptive convenience only and does not limit the present disclosure to the scope of the embodiments cited. It can be understood that for those skilled in the art, after understanding the principle of the system, it may be possible to make any combination of the modules or form subsystems to connect with other modules without departing from this principle. In some embodiments, the generation module 210, the instruction determination module 220, and the processing module 230 may be different modules in one system, or one module may implement the functions of two or more of the above modules. For example, each module may share a common storage module, or each module may have its own storage module. Variations such as these are within the scope of protection of the present disclosure.

Figure 3:
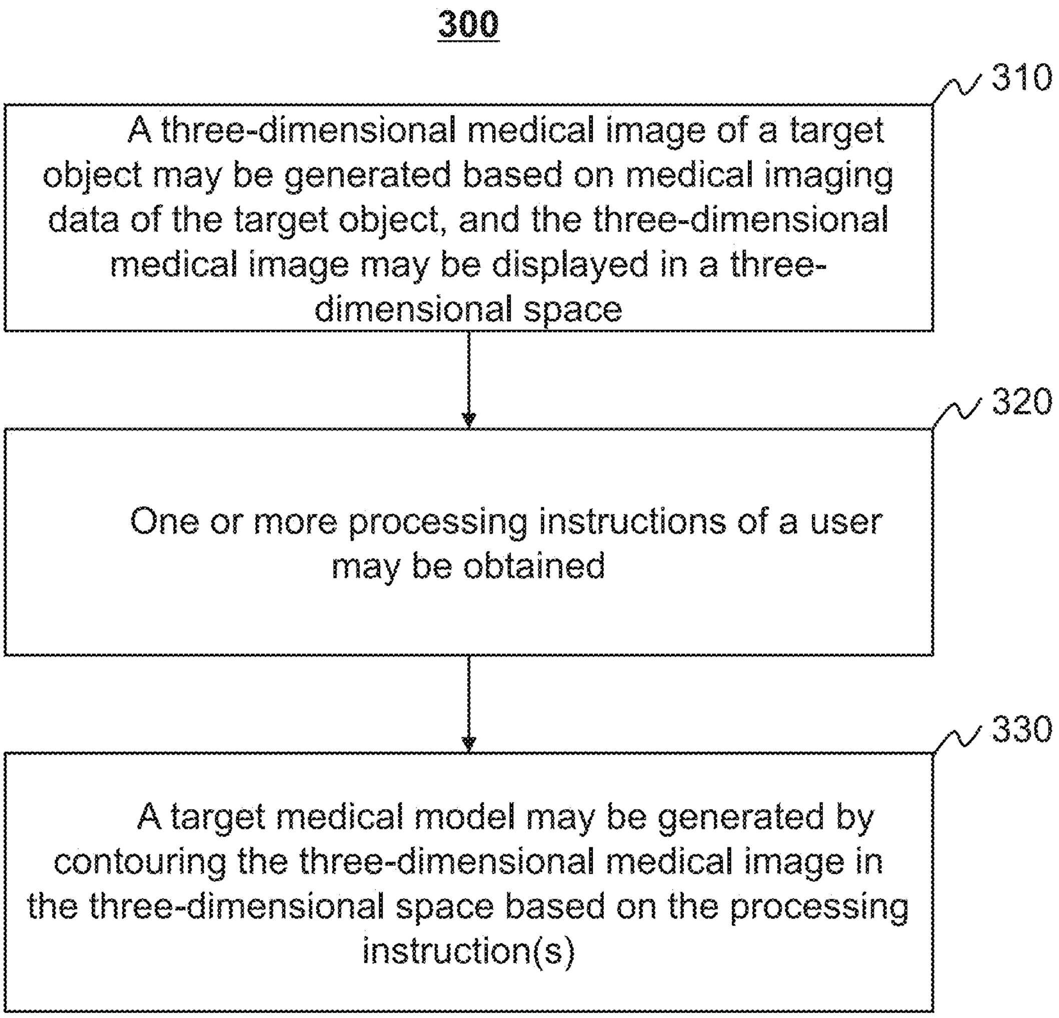
FIG. 3 is a flowchart illustrating an exemplary process for processing a three-dimensional image according to some embodiments of the present disclosure.

FIG. 3 is a flowchart illustrating an exemplary process for processing a three-dimensional image according to some embodiments of the present disclosure. In some embodiments, the process 300 for processing a three-dimensional image may be performed by the system 100 (e.g., the processing device 130) or the system 200. For example, the process 300 may be stored in a storage device (e.g., the storage device 150) in the form of a program or instructions, and the process 300 may be implemented when the processing device 130 or the system 200 executes the program or instructions. The schematic diagram of the operation of the process 300 presented below is illustrative. In some embodiments, one or more additional operations not described and/or one or more operations not discussed may be utilized to complete the process. Further, the order of operations of the process 300 illustrated in FIG. 3 and described below is not limiting.

In 310, a three-dimensional medical image of a target object may be generated based on medical imaging data of the target object, and the three-dimensional medical image may be displayed in a three-dimensional space. In some embodiments, 310 may be performed by the generation module 210.

The target object is an object that is subjected to an imaging scan. In some embodiments, the target object may include a biological object (e.g., a human body, an animal, etc.), a non-biological object (e.g., a body mold), etc. In some embodiments, the target object may include a specific part of the body, e.g., the head, neck, chest, etc., or any combination thereof. In some embodiments, the target object may include a specific organ, e.g., a liver, kidney, pancreas, etc., or any combination thereof. In some embodiments, the target object may include a region of interest (ROI), e.g., a tumor, a nodule, etc.

The three-dimensional medical image is a three-dimensional image reflecting internal information of the target object. For example, if the target object is a patient's lung, the three-dimensional medical image is a three-dimensional image of the patient's lung. The three-dimensional medical image may visualize a size, shape, contour, etc., of the target object or its components in the three-dimensional space.

In some embodiments, the three-dimensional medical image may include a lesion region of the target object. The three-dimensional medical image in such embodiments may visually reflect a size, shape, contour, spatial position, etc., of the lesion region in the three-dimensional space.

In some embodiments, the three-dimensional medical image may be generated based on medical imaging data of the target object.

The medical imaging data is data generated by scanning the target object using at least one medical imaging device.

In some embodiments, the medical imaging data may include a three-dimensional body data set of the target object or a plurality of two-dimensional medical image sequences.

In some embodiments, the medical imaging data may be one of CT imaging data, MR imaging data, X-ray imaging data, PET imaging data, SPECT imaging data, or fused image data including multiple image data. For example, if the target object is a patient's lung, and the medical imaging data of the target object may be the CT imaging data of the lung. The CT imaging data of the lung may be generated by performing a CT scan on the lung of the patient to obtain CT scanning data, and reconstructing the CT imaging data.

In some embodiments, the medical imaging data may be pre-stored in a storage device (e.g., the storage device 150), and the generation module 210 may retrieve the medical imaging data directly from the storage device.

In some embodiments, the target object may be scanned by a medical imaging device to obtain scanning data of the target object. Based on the scanning data, the medical imaging data of the target object may be obtained through reconstruction. For example, the medical imaging data may be obtained by scanning the target object by an MRI scanner, a CT scanner, and/or a PET scanner, and may be reconstructed based on the scanning data. For more information about the medical imaging device, please refer to FIG. 1 and its related description.

In some embodiments, the medical imaging data may be displayed in the three-dimensional space.

The three-dimensional medical image may be generated in a variety of ways. In some embodiments, if the medical imaging data includes data of a sequence of multiple two-dimensional medical images, the generation module 210 may perform a three-dimensional reconstruction of the medical imaging data to obtain a three-dimensional medical image of the target object.

In some embodiments, in the generation of the three-dimensional medical image, different display parameters may be used for different tissues in the three-dimensional medical image.

A display parameter may be referred to as a parameter used to display a tissue in the three-dimensional medical image. For example, the display parameter may include a color (e.g., RGB value), a transparency (e.g., Alpha value), etc. The display parameter may be determined in a variety of ways. For example, the display parameter may be determined by a user input, etc.

In some embodiments, the generation module 210 may determine the display parameter of at least one tissue in the three-dimensional medical image based on a tissue type and/or a spatial position relationship between different tissues in the medical imaging data.

The tissue refers to an organ tissue. The tissue type may include, but is not limited to, a liver, a kidney, a pancreas, etc. The spatial position relationship between different tissues refers to the distribution of different organ tissues in the body. For example, the anterior, posterior, and lateral sides of the lungs are facing the ribs or chest wall, the mediastinum is in the medial side of the lungs, the pleura is at the upper part of the lungs, and the diaphragm is at the lower part of the lungs.

In some embodiments, the at least one tissue may include a target tissue.

The target tissue is an organ tissue in which the position of a lesion is located. The target tissue may be determined based on the condition of the target subject. For example, the target tissue may be determined by a physician based on the position and/or size of the patient's tumor, or may be determined automatically by the system based on the condition.

In some embodiments, the at least one tissue may further include a related tissue.

The related tissue is a tissue that is related to the target tissue. For example, the related tissue may be a normal tissue covering the target tissue, e.g., a normal tissue oriented anteriorly, posteriorly, laterally, medially, above, below, etc., of the target tissue.

In some embodiments, the generation module 210 may determine the display parameter of the at least one tissue in the three-dimensional medical image by a first preset rule based on the tissue type and/or the spatial position relationship between the different tissues in the medical imaging data.

In some embodiments, the first preset rule may include that an Alpha value in the display parameter of the target tissue is set to be lower than a first threshold and an Alpha value in the display parameter of the related tissue is set to be higher than a second threshold. In some embodiments, the first preset rule may further include that an RGB value in the display parameter of the target tissue is set to be different from an RGB value in the display parameter of the related tissue.

In some embodiments, the first preset rule may include that an Alpha value in the display parameter of a front side surface of the target tissue is set larger than the second threshold when the lesion position is located inside the target tissue and the lesion position is obscured by the front side surface (i.e., a surface close to the user's side), a back side surface (i.e., a surface away from the user's side), etc., of the target tissue.

Figure 11A:
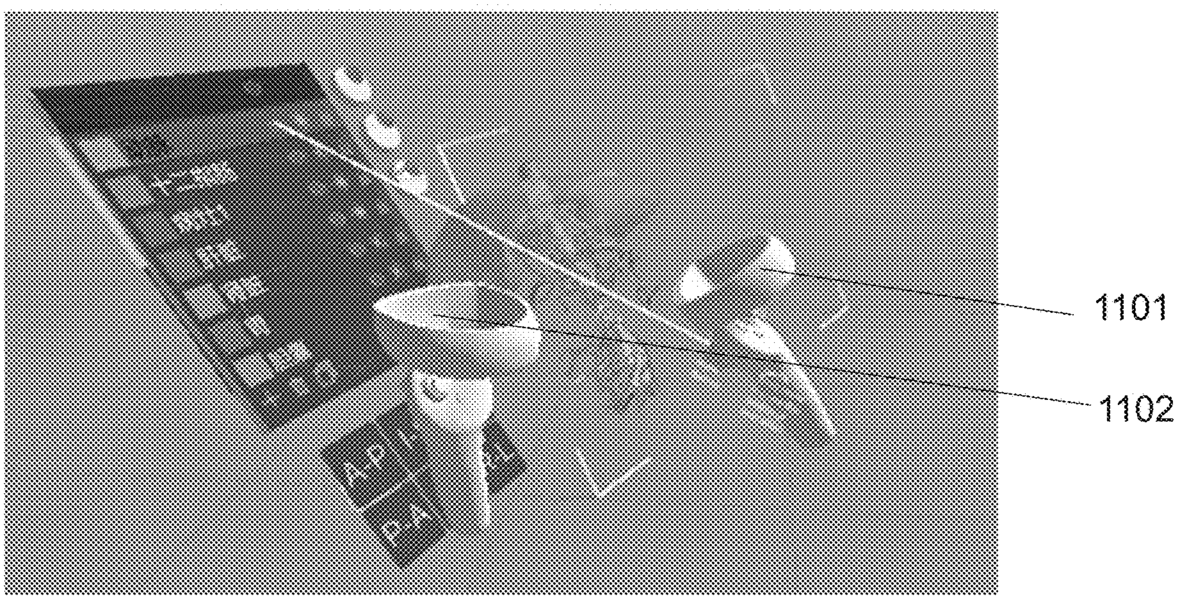
FIGS. 11A-11D are schematic diagrams illustrating exemplary three-dimensional medical models according to some embodiments of the present disclosure.
Figure 11B:
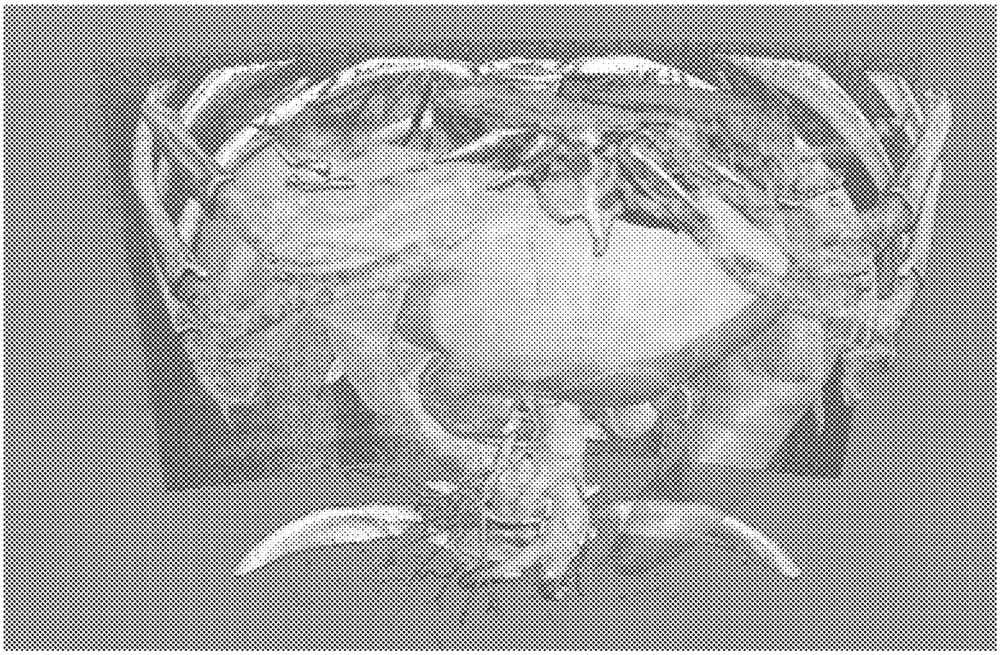
Figure 11C:
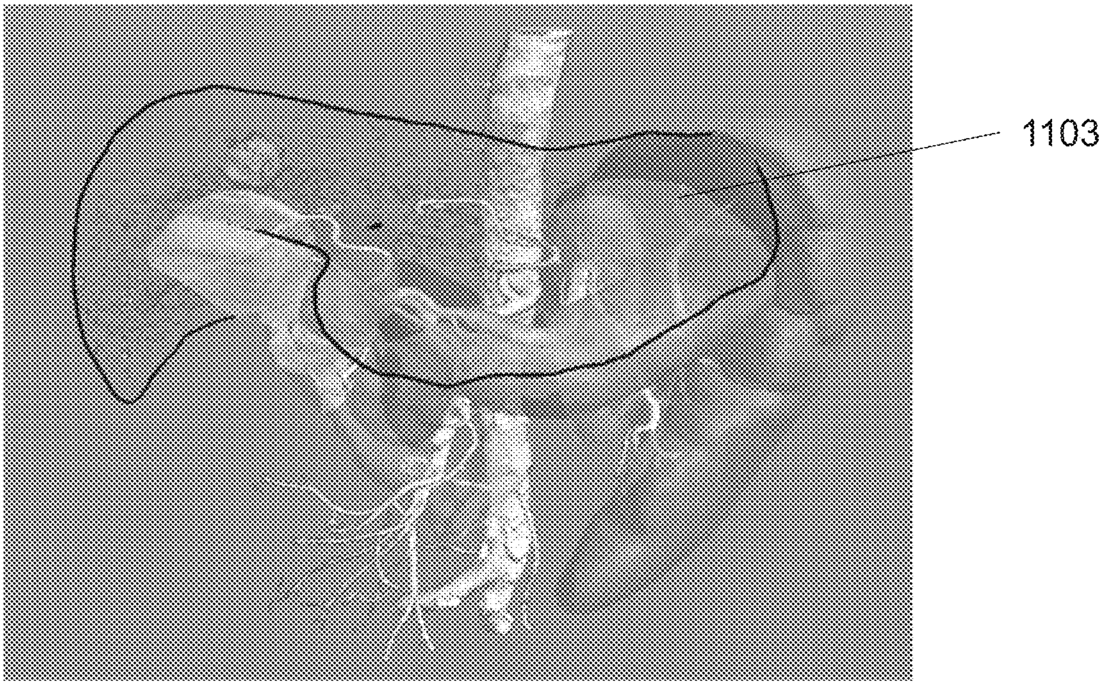

It should be noted that when the Alpha value is set below the first threshold, the tissue or a portion of the structure is opaque, which is more visible (also referred to as highlighting). When the Alpha value is set larger than the second threshold, the tissue or a portion thereof is transparent, which is less visible (also referred to as hidden display). As shown in FIGS. 11B-11C, the tissue or a portion thereof is opaque and highly visible, which is highlighted (see FIG. 11B), while the tissue 1103 or a portion thereof is transparent and less visible, which is hidden (see FIG. 11C).

In some embodiments, the first preset rule may further include the display parameter of the at least one tissue in the three-dimensional medical image is determined by a machine learning model. In a specific embodiment, the generation module 210 may determine the display parameter(s) of the at least one tissue in the three-dimensional medical image by a display parameter determination model. Specifically, the medical imaging data of the target object may be processed by the display parameter determination model to determine the display parameter(s) of the at least one tissue in the three-dimensional medical image.

The display parameter determination model may be a machine learning model. For example, the display parameter determination model may be a convolutional neural network (CNN) model.

In some embodiments, an input of the display parameter determination model may include the medical imaging data of the target object, and an output may include the display parameter(s) of the at least one tissue in the three-dimensional medical image.

In some embodiments, the display parameter determination model may be obtained based on training a large number of first training samples with first labels. An exemplary training process may include inputting the first training samples into an initial display parameter determination model, constructing a loss function based on a model output and the first labels, and iteratively updating the initial display parameter determination model based on the loss function until a preset condition is met and the training is terminated, resulting in a trained display parameter determination model. The preset condition may be that the loss function is less than a threshold, convergence, or a count of the training iterations reaches a threshold.

In some embodiments, the first training samples may include the medical imaging data of the sample object, and the first labels may include an actual display parameter of at least one tissue in the three-dimensional medical image of a sample object. The first training samples and the first labels may be determined based on data from a historical contour of the sample object.

In some embodiments, if the medical imaging data includes a three-dimensional body data set of the target object, the generation module 210 may determine the display parameter(s) of the at least one tissue in the three-dimensional medical image by a second preset rule.

In some embodiments, the second preset rule may include that the display parameter(s) of the at least one tissue in the three-dimensional medical image are determined based on a value domain and a spatial domain of the medical imaging data. The value domain may include values corresponding to voxels in the medical imaging data. For example, if the medical imaging data includes CT imaging data, the values corresponding to the voxels may include an X-ray attenuation value. The spatial domain may include values corresponding to spatial positions of voxels in the medical imaging data.

In some embodiments, the second preset rule may include that an RGB value and an Alpha value of each voxel are determined based on the value domain and an Alpha value of each voxel is determined based on the spatial domain. In a specific embodiment, the second preset rule may include that the value domain of each voxel in the medical imaging data is determined based on a correspondence (between a reference value domain, a reference RGB value, and a reference Alpha value), and then the RGB value and Alpha value of each voxel are determined based on the value domain. In a specific embodiment, the second preset rule may include that the Alpha value of the voxel in the medical imaging data whose spatial domain is greater than a spatial domain threshold is set as higher than the second threshold, and the Alpha value of the voxel in the medical imaging data whose spatial domain is less than the spatial domain threshold is set as lower than the first threshold. For more information about the first threshold and the second threshold, please refer to the previous description.

In some embodiments, the display parameter(s) of the at least one tissue in the three-dimensional medical image may be adjusted by the user.

In some embodiments of the present disclosure, by determining the display parameter(s) of the at least one tissue, a tissue of interest to the user, such as a tissue in which a lesion region is located, may be visually displayed, and a tissue of no interest to the user, such as a normal tissue overlying the target tissue or a normal tissue at a distance from the target tissue, may be hidden, allowing the user to visualize the lesion region.

In some embodiments, the display parameter(s) may further include a texture parameter of the tissue. In some embodiments, the texture parameter may be determined based on a curved degree of the tissue. In some embodiments, the texture parameter may also be determined by the user or the system, without limitation herein. The texture parameter may highlight a three-dimensional structure of the tissue, further facilitating visual observation for the user.

In some embodiments, the three-dimensional medical image may include a three-dimensional rendered image, and the three-dimensional rendered image may be generated based on the medical imaging data.

In some embodiments, the generation module 210 may perform a three-dimensional rendering of the medical imaging data of the target object to generate the three-dimensional rendered image. For example, the generation module 210 may process the medical imaging data of the target object by denoising, filtering outliers, adjusting a range of value distribution, interpolating or down-sampling, fusing with other voxel data, etc., set an appropriate display parameter to show a region of interest, and generate the image by using a direct voxel rendering or an indirect voxel rendering, etc., to obtain the three-dimensional rendered image. The three-dimensional rendering can display raw data of each voxel in three dimensions.

In some embodiments, the generation module 210 may also perform a two-dimensional rendering of the medical imaging data of the target object to obtain a two-dimensional rendered image. In some embodiments, the two-dimensional rendered image and the three-dimensional rendered image may be displayed in combination in the three-dimensional space. For more information about the two-dimensional rendered image, please refer to FIG. 5 and its related description.

In some embodiments, the generation module 210 may segment the medical imaging data of the target object based on a segmentation algorithm to obtain imaging data subsets of multiple tissues. Exemplary segmentation algorisms may include, but is not limited to, an octree based split-merge algorithm, an adaptive wraparound box based split-merge algorithm, etc. Further, the generation module 210 may separately render the imaging data subsets in three dimensions according to different display parameters to obtain the three-dimensional rendered image. As shown in FIG. 11B, the three-dimensional rendered image obtained by the three-dimensional rendering may visually display information such as contours, shapes and structures of different tissues.

In some embodiments, the three-dimensional space may be real, such as the real world. Alternatively, the three-dimensional medical image may be virtual. Accordingly, the generation module 210 may project and display the three-dimensional medical image of the target object in the real world via a relevant device (e.g., a VR device, an AR device, etc.).

In some embodiments, the three-dimensional space may be virtual, such as a three-dimensional space in a displayer. The three-dimensional medical image may be a virtual image. Accordingly, the generation module 210 may display the three-dimensional medical image of the target object in the displayer of a relevant device (e.g., a mobile device, a tablet device, etc.).

In some embodiments, the generation module 210 may display one or more of the three-dimensional medical image and the three-dimensional rendered image in the three-dimensional space.

In 320, one or more processing instructions of a user may be obtained. In some embodiments, 310 may be performed by the instruction determination module 220.

A processing instruction may refer to an instruction for performing a processing operation on the three-dimensional medical image. For example, the processing instruction may be an instruction to perform a contouring operation on the three-dimensional medical image.

The processing instruction(s) may be obtained in a variety of ways. In some embodiments, the processing instruction(s) may be obtained by a user input via a cursor component. The cursor component may be a component that performs an actual contouring operation on the three-dimensional medical image. The cursor component may be a virtual component or a physical component.

In some embodiments, the user may input the processing instruction(s) through at least one cursor component. For example, the user may input the processing instruction through one cursor component to control a display view angle, a display size, and/or to edit content in the three-dimensional medical image, etc. As another example, the user may input different processing instructions through two cursor components, such as one cursor component for controlling the display view angle, the display size, etc., and the other cursor component for content editing, etc.

In some embodiments, the cursor component may include at least one shortcut key for a quick processing of the three-dimensional medical image. For example, the shortcut key can be used to make quick and accurate adjustment(s) to value(s), avoiding error(s) caused by adjusting the value(s) remotely, etc.

In some embodiments, the user may contour the three-dimensional medical image directly in the three-dimensional space by holding the cursor component, which may be displayed in the three-dimensional space. In some embodiments, the user may edit the three-dimensional medical image by at least one shortcut key to achieve operations such as push painting, engraving, erasing, etc.

In some embodiments, the processing instruction(s) may be obtained by identifying the user posture. For more information about the obtaining the processing instruction, please refer to FIG. 10 and its related description.

In some embodiments, the user may also input the processing instruction(s) via a mouse.

In 330, a target medical model may be generated by contouring the three-dimensional medical image in the three-dimensional space based on the processing instruction(s). In some embodiments, 310 may be performed by the processing module 230.

The target medical model is a medical model obtained after processing. In some embodiments, the medical model is a three-dimensional model. The medical model may be used to visualize the size, shape, contour, etc., of the target object or its components in the three-dimensional space.

In some embodiments, the target medical model may include three-dimensional contour information. The three-dimensional contour information may visually reflect a three-dimensional contour, shape, etc., of the target object. In some embodiments, the three-dimensional contour information may include a contour of a region of interest (ROI) and/or a contour of a point of interest (POI).

In some embodiments, the processing module 230 may determine a radiotherapy plan based on the three-dimensional contour information. For example, the three-dimensional contour information may include a POI of a lesion region and a POI of a non-lesion region. In determining the radiotherapy plan, the radiation plan may be determined based on the POI of the lesion region and the POI of the non-lesion region. Exemplarily, radiation-related parameters such as a radiation dose, a position, and an angle may be determined based on the POI of the lesion region, a radiation amount in the non-lesion region during the radiation process may be simulated based on the radiation-related parameters, and the radiation-related parameters may be adjusted based on a simulation result, so that the radiation amount in the lesion region meets the treatment requirements and the radiation amount in the non-lesion region is below a safety threshold.

In some embodiments, the target medical model may include target area contour information (also referred to as contour information of a target area).

The target area contour information may include information obtained by contouring of the lesion region of the target object. In some embodiments, the target area contour information may include an area size and/or shape of the target area, etc. The target area contour information may be visually reflected on the target medical model. For example, the target medical model may be visualized according to a specific display parameter. In some embodiments, the target area contour information may be displayed on the target medical model in a two-dimensional or three-dimensional format.

In some embodiments, the processing module 230 may contour the three-dimensional medical image in the three-dimensional space based on the processing instruction, and a contouring result may be displayed and stored in the form of a three-dimensional model (i.e., the target medical model).

In some embodiments, the processing instruction(s) may include perform contouring for the lesion region of the target object, and accordingly, the processing module 230 may determine a contour of the lesion region in the three-dimensional medical image based on the processing instruction(s). In some embodiments, the processing instruction(s) may include expanding the lesion region of the target object, and accordingly, the processing module 230 may automatically expand the lesion region in the three-dimensional medical image based on the processing instruction(s). For more information about a range of the expansion, please refer to FIG. 6 and its description.

In some embodiments, the contouring may be performed based on exemplary algorithms including a visual resolution algorithm, a standard-uptake-value (SUV) peak relative percentage algorithm, a target area/benchmark SUV ratio algorithm, and various other algorithms based on mathematical formula.

In some embodiments, the processing module 230 may also perform contouring for a two-dimensional plane in the three-dimensional space, and accordingly, the target medical model may include two-dimensional contour information. For more information about the two-dimensional contour information, please refer to FIG. 4 and its related description.

In some embodiments, the processing module 230 may obtain the initial medical model; generate the target medical model by processing the initial medical model in the three-dimensional space based on the processing instruction(s). For more information about the generating the target medical model based on the initial medical model, please refer to FIG. 6 and its related description.

In some embodiments of the present disclosure, by directly displaying the three-dimensional medical image of the target object in the three-dimensional space, it enables the radiotherapist to directly browse and modify data in the three-dimensional space based on operation(s) consistent with human habits, thereby improving the convenience of interaction and work efficiency. At the same time, by determining the display parameters of different voxels or tissues in the medical imaging data, different colors and/or transparencies can be used to visualize and highlight different voxels or tissues for the radiotherapists to observe them intuitively.

Figure 4:
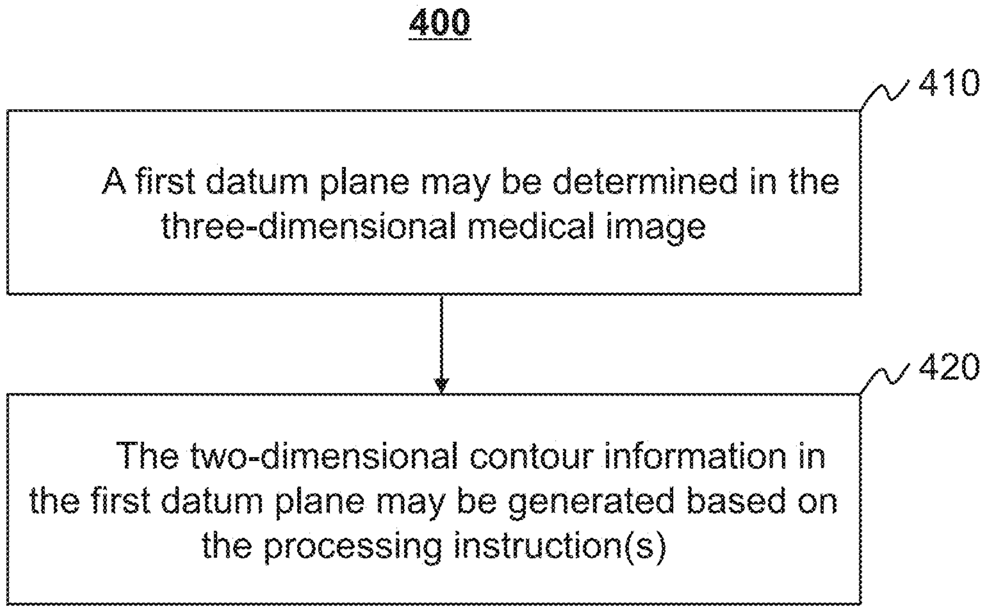
FIG. 4 is a flowchart illustrating an exemplary process for generating two-dimensional contour information according to some embodiments of the present disclosure.

FIG. 4 is a flowchart illustrating an exemplary process for generating two-dimensional contour information according to some embodiments of the present disclosure. In some embodiments, the process 400 may be executed by the system 100 (e.g., the processing device 130) or the system 200 (e.g., the processing module 230). For example, the process 400 may be stored in a storage device (e.g., the storage device 150) in the form of a program or instructions, and the process 400 may be implemented when the processing device 130 or the processing module 230 executes the program or instructions. The schematic diagram of the operation of the process 400 presented below is illustrative. In some embodiments, one or more additional operations not described and/or one or more operations not discussed may be utilized to complete the process. Further, the order of operations of the process 400 illustrated in FIG. 4 and described below is not limiting.

In 410, a first datum plane may be determined in the three-dimensional medical image.

The first datum plane may be a two-dimensional tangent plane. The first datum plane may be a two-dimensional tangent plane at any angle determined in the three-dimensional medical image.

The first datum plane may be used to determine two-dimensional contour information. The two-dimensional contour information may include information obtained by contouring for a lesion region of the target object in the first datum plane. The lesion region of the target object may be a two-dimensional region in the first datum plane.

The first datum plane may be determined in a variety of ways. In some embodiments, the processing module 230 may determine the first datum plane in the three-dimensional medical image by determining a cut point position and/or a cut plane direction, determining the first datum plane based on the cut point position and/or the cut plane direction, and recommending the first datum plane to the user. In some embodiments, a center point of the lesion region of the target object may be determined as the cut point position. In some embodiments, an angle that visually reflects the lesion region may be determined as the cut plane direction. For example, an angle parallel to the top of the head may be determined as the cut plane direction.

In some embodiments, the processing module 230 may determine the first datum plane of the target object in the three-dimensional medical image based on historical data. For example, the processing module 230 may retrieve a historical object in the database that is similar to the condition of the target object, determine a historical first datum plane in historical contour data of the historical object as the first datum plane of the target object, and recommend the first datum plane to the user.

In some embodiments, the first datum plane may also be determined by the user and is not limited herein.

In 420, the two-dimensional contour information in the first datum plane may be generated based on the processing instruction(s).

In some embodiments, the two-dimensional contour information may include a size, shape, contour, etc., of a region. The two-dimensional contour information may be visually reflected on a cross-sectional image corresponding to the first datum plane. For example, the two-dimensional contour information may be displayed on the cross-sectional image according to a specific display parameter.

In some embodiments, the processing module 230 may contour, based on the processing instruction(s), the cross-sectional image corresponding to the first datum plane to obtain the two-dimensional contour information. The contouring is performed in the same manner as the contouring of the three-dimensional medical image in the three-dimensional space, and for more information, please refer to FIG. 3 and its related description, which is not repeated herein.

In some embodiments, the two-dimensional contour information may be displayed in the three-dimensional space.

In some embodiments, the processing module 230 may simultaneously display the three-dimensional medical image and the cross-sectional image in the first datum plane in the three-dimensional space, and the target medical model obtained by contouring the three-dimensional medical image and the two-dimensional contour information obtained by contouring the cross-sectional image may be displayed in the three-dimensional space at the same time.

In some embodiments, the processing module 230 may determine a radiotherapy plan based on the two-dimensional contour information. For example, the two-dimensional contour information may include a POI of a lesion region and a POI of a non-lesion region. When determining the radiotherapy plan, the radiation plan may be determined based on the POI of the lesion region and/or the POI of the non-lesion region. Determining the radiotherapy plan based on the two-dimensional contour information is similar to determining the radiotherapy plan based on the three-dimensional contour information, which can be found in 330 in FIG. 3.

In some embodiments of the present disclosure, a structure, a position, and/or a size of a lesion region may be visualized by displaying both the three-dimensional medical image and a cross-sectional image in a certain plane in the three-dimensional space to facilitate observation by the radiotherapist. Also, displaying a certain layer of the cross-sectional image can facilitate better observation of lossless texture information, and take advantage of the radiotherapist's past experience in processing on the two-dimensional plane.

Figure 5:
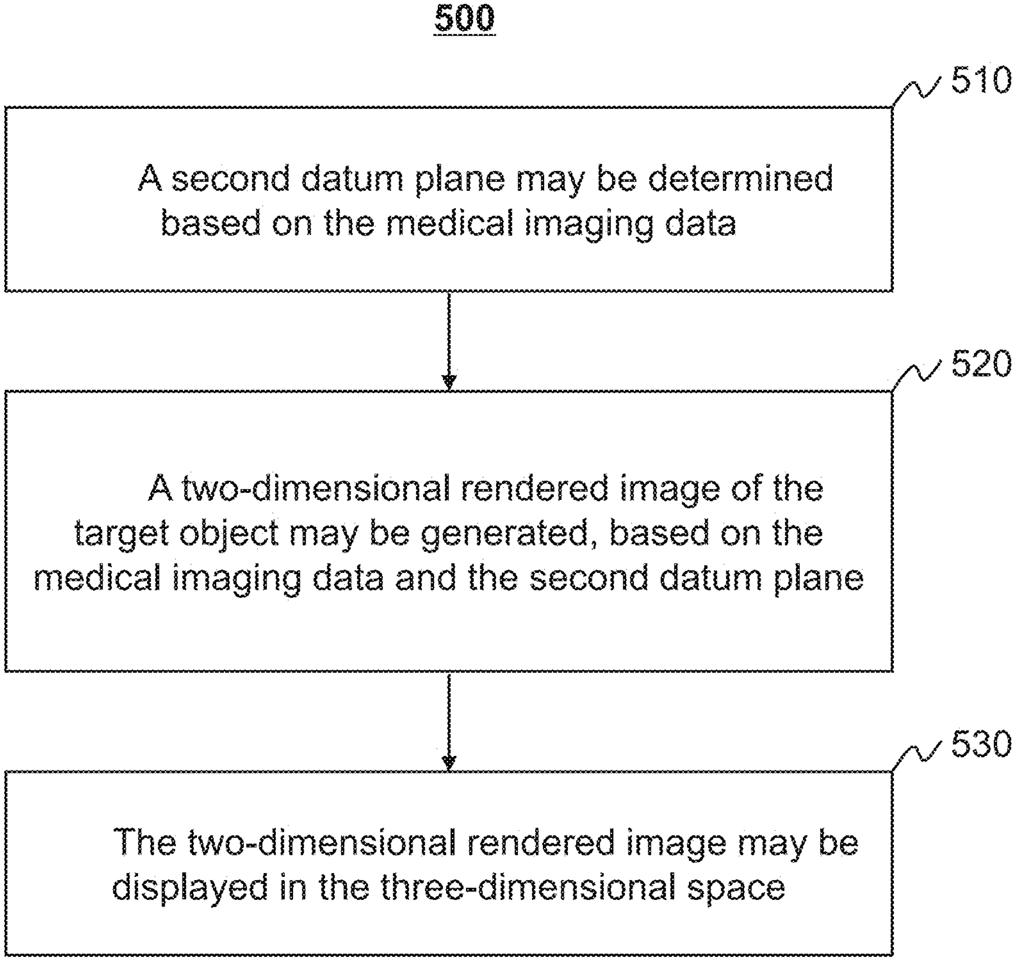
FIG. 5 is a flowchart illustrating an exemplary process for generating a two-dimensional rendered image according to some embodiments of the present disclosure.

FIG. 5 is a flowchart illustrating an exemplary process for generating a two-dimensional rendered image according to some embodiments of the present disclosure. In some embodiments, the process 500 may be executed by the system 100 (e.g., the processing device 130) or the system 200 (e.g., the generation module 210). For example, the process 500 may be stored in a storage device (e.g., the storage device 150) in the form of a program or instructions, and the process 500 may be implemented when the processing device 130 or the generation module 210 executes the program or instructions. The schematic diagram of the operations of the process 500 presented below is illustrative. In some embodiments, one or more additional operations not described and/or one or more operations not discussed may be utilized to complete the process. Further, the order of operations of the process 500 illustrated in FIG. 5 and described below is not limiting.

In 510, a second datum plane may be determined based on the medical imaging data.

The second datum plane may be a two-dimensional plane. The second datum plane may be a two-dimensional plane at any angle determined in the medical imaging data.

The second datum plane may be used to generate a two-dimensional rendered image. The two-dimensional rendered image may be an image obtained after performing a two-dimensional rendering.

The second datum plane is determined in a manner similar to the determination of the first datum plane, which can be found in FIG. 4 and its related description, and is not repeated herein.

In 520, a two-dimensional rendered image of the target object may be generated, based on the medical imaging data and the second datum plane. In 530, the two-dimensional rendered image may be displayed in the three-dimensional space.

In some embodiments, the generation module 210 may generate a two-dimensional rendered image of the target object based on a two-dimensional rendering of at least a portion of the medical imaging data in the second datum plane. The two-dimensional rendering may enable a two-dimensional display of raw data of each pixel.

Figure 11D:
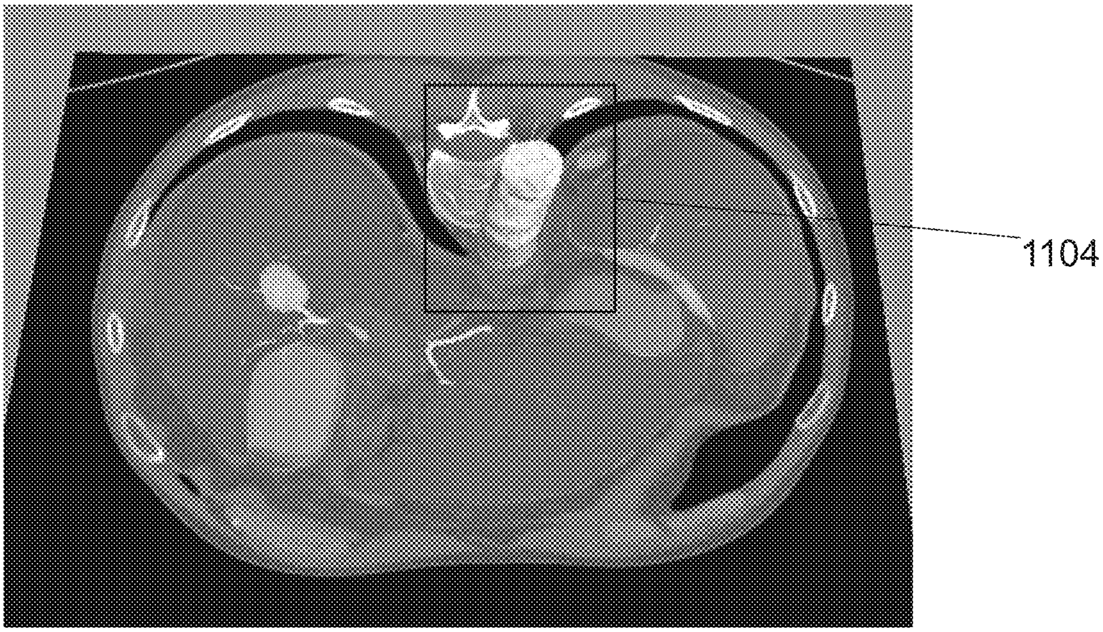

In some embodiments, the two-dimensional rendered image and the three-dimensional rendered image may be displayed in combination in the three-dimensional space. As shown in FIG. 11D, a corresponding portion of box 1104 includes the three-dimensional rendered image obtained by rendering the blood vessel in three dimensions, and the remaining portion includes the two-dimensional rendered image obtained by the two-dimensional rendering.

In some embodiments, the processing module 230 may, based on the processing instruction(s), contour the two-dimensional rendered image corresponding to the second datum plane to obtain the two-dimensional contour information. The contouring is performed in the same manner as the contouring of the three-dimensional medical image in the three-dimensional space, and for more information, please refer to FIG. 3 and its related description, which is not repeated here.

In some embodiments of the present disclosure, by determining and displaying the two-dimensional rendered image in the three-dimensional space, processing of the lesion region of the target object by the radiotherapist may be facilitated in conjunction with past experience in processing in the two-dimensional plane.

Figure 6:
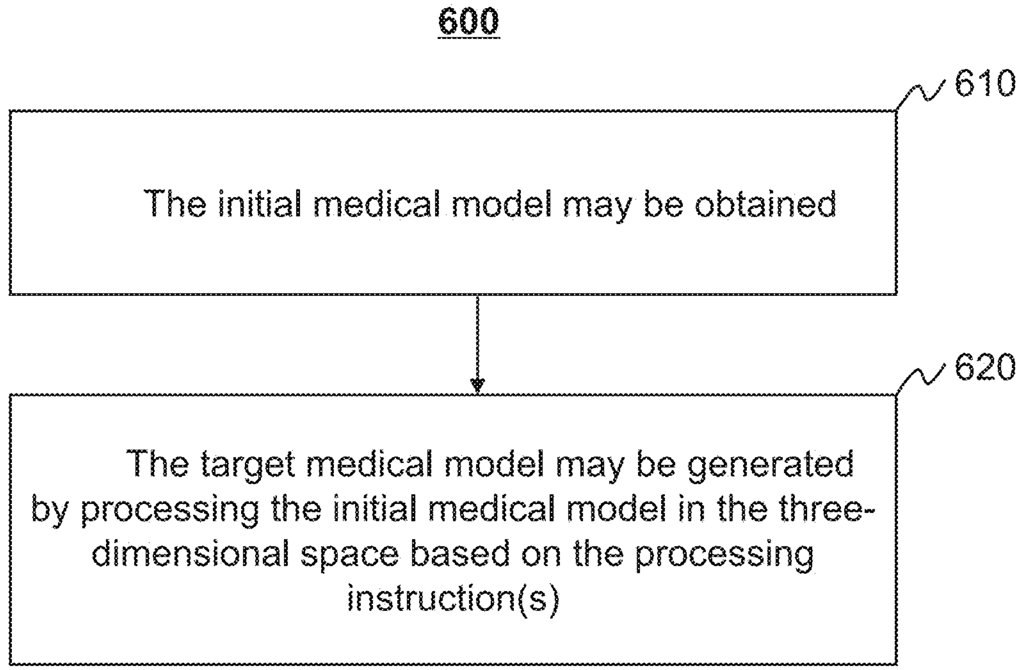
FIG. 6 is a flowchart illustrating an exemplary process for generating a target medical model according to some embodiments of the present disclosure.

FIG. 6 is a flowchart illustrating an exemplary process for generating a target medical model according to some embodiments of the present disclosure. In some embodiments, the process 600 may be executed by the system 100 (e.g., the processing device 130) or the system 200. For example, the process 600 may be stored in a storage device (e.g., the storage device 150) in the form of a program or instruction, and the process 600 may be implemented when the processing device 130 or the system 200 executes the program or instructions. The schematic diagram of the operation of the process 600 presented below is illustrative.

In some embodiments, one or more additional operations not described and/or one or more operations not discussed may be utilized to complete the process. Further, the order of operations of the process 600 illustrated in FIG. 6 and described below is not limiting.

In 610, the initial medical model may be obtained. In some embodiments, 610 may be performed by the generation module 210.

The initial medical model may refer to an initial medical model of the target object. In some embodiments, the initial medical model may be a medical model that has been constructed without further processing (e.g., contouring, etc.). In such embodiments, the initial medical model may be a three-dimensional model, which is specifically represented as a three-dimensional image of the target object. The initial medical model may visually reflect a size, shape, contour, etc., of the target object or its components in the three-dimensional space.

The initial medical model may be obtained in a variety of ways. In some embodiments, the initial medical model may be constructed based on the medical imaging data of the target object.

In some embodiments, the generation module 210 may process the medical imaging data of the target object based on a three-dimensional modeling technique to obtain the initial medical model of the target object. Exemplary three-dimensional modeling techniques may include a virtual reality (VR) technique, an augmented reality (AR) technique, etc. For more information about the medical imaging data, please refer to FIG. 3 and its related description.

In some embodiments, the generation module 210 may process imaging data subsets of multiple tissues of the target object based on the three-dimensional modeling technique to determine an initial medical sub-model corresponding to each tissue. For more information about the imaging data subsets, please refer to FIG. 3 and its related description.

In some embodiments, the generation module 210 may determine a target region based on the medical imaging data; generate the initial medical model based on a preset processing range and the target region.

The target region may be a lesion region. The target region may be a three-dimensional region. In some embodiments, the target region may be a tumor target region (GTV) of the target object. The target region may be determined by the user, or by the system.

The preset processing range may be a range over which the target region is expanded. In some embodiments, the preset processing range may be 0, i.e., no expansion of the target region is performed.

The preset processing range may be obtained in a variety of ways. In some embodiments, the user may determine the preset processing range based on a priori knowledge, the underlying condition of the lesion region, etc.

In some embodiments, the generation module 210 may divide the target region into multiple three-dimensional sub-regions and determine a processing sub-region of each three-dimensional sub-region based on a range determination model. The multiple processing sub-regions may be fused to obtain the preset processing range.

The three-dimensional sub-region may refer to a portion of the spatial region in the target region. The processing sub-range may refer to a range where the three-dimensional sub-region is expanded.

In some embodiments, the generation module 210 may determine feature vectors corresponding to the multiple voxels in the target region, and cluster the feature vectors based on a clustering algorithm to obtain multiple sets of clustering centers. Each set of clustering centers may be a three-dimensional sub-region. The clustering algorithm may be a K-mean clustering or any other algorithm. The operation may be performed in advance.

Elements of the feature vectors may correspond to the medical imaging data. The feature vectors may be determined in a variety of ways based on the medical imaging data. In some embodiments, the elements of the feature vectors may correspond to a number of blood vessels, a number of surrounding tissues, a distance to surrounding tissues, etc., in the medical imaging data. For example, the feature vectors may be (a, b, c), where a indicates the number of blood vessels, b indicates the number of surrounding tissues, c indicates the distance to the surrounding tissues, etc.

The range determination model may be a machine learning model. For example, the range determination model may be a deep neural network (DNN) model, etc.

In some embodiments, an input of the range determination model may include an object feature of the target object, a lesion feature of the target region, and a region feature corresponding to each of the multiple three-dimensional sub-regions, and an output is a processing sub-range of each of the multiple three-dimensional sub-regions.

The object feature may refer to a feature related to the target object. The object feature may include a gender, an age, a weight, a height, a currently suffered disease, a historically suffered disease, etc., of the target subject.

The lesion feature may refer to a feature related to the target region. The lesion feature may include an organ and/or tissue in which the lesion is located, a size of the lesion, etc. The lesion feature may be determined based on the medical imaging data. For example, the medical imaging data may be processed by an embedding layer to obtain the lesion feature. The processing of the embedding layer is essentially a process of extracting depth information. In some embodiments, the embedding layer may be obtained by a joint training with the range determination model.

In some embodiments, the medical imaging data may be input into the model instead of the lesion feature. In some embodiments, the medical imaging data corresponding to the target region may be input into the model instead of the lesion feature.

The region feature may refer to a feature related to a three-dimensional sub-region. The region feature may include a size, a spatial position, a shape, etc., of the three-dimensional sub-region.

In some embodiments, the range determination model may be obtained by training an initial range determination model using a large number of second training samples with second labels. An exemplary training process may include: inputting the second training samples into the initial range determination model, constructing a loss function based on a model output and the second labels; iteratively updating the initial range determination model based on the loss function until a preset condition is met and the training is terminated, resulting in a trained range determination model. The preset condition may be that the loss function is less than a threshold, convergence, or a count of the training iterations reaches a threshold.

In some embodiments, the range determination model may be obtained by a joint training with the embedding layer. An exemplary joint training process may include: inputting medical imaging data of a sample object into an initial embedding layer; obtaining a lesion feature of the initial embedding layer outputting the sample object corresponding to a sample target region; inputting the lesion feature of the sample target region, and the object feature of the sample object, and the region feature corresponding to each of a plurality of three-dimensional sub-regions in the sample target region into the initial range determination model; constructing a loss function based on the output of the initial range determination model and the second labels; iteratively updating parameters of the initial embedding layer and the initial range determination model based on the loss function until a preset condition is met, then the training may be terminated, and the trained range determination model and the embedding layer may be obtained.

In some embodiments, the second training samples may include an object feature of the sample object, a lesion feature of the sample object corresponding to the sample target region, a region feature of the sample target region corresponding to each of the multiple three-dimensional sub-regions, and the second labels may include a processing sub-range corresponding to each of the multiple three-dimensional sub-regions. The second training samples and the second labels may be determined based on data generated by historical segmentation of the sample target region of the sample object.

The obtaining of the parameter(s) of the embedding layer using the above training process is beneficial in some cases to solve the problem of difficulty in obtaining labels when training the embedding layer alone, and also enables the embedding layer to obtain a feature that reflects the lesion region better.

After determining a preset expansion range, the processing module 230 may generate the initial medical model by expanding based on the preset processing range, a three-dimensional shape of the target region.

In some embodiments, a range of the initial medical model may be further adjusted based on an operation of the user. For example, the initial medical model may be further adjusted to a medical model corresponding to a clinical target region (CTV) or a planned target region (PTV) based on the operation of the user.

In some embodiments, the operation of the user may include making a specific posture or pressing a specific key, etc. In some embodiments, the generation module 210 may identify the user posture in order to further adjust the range of the initial medical model. For example, if the user posture corresponds to an operation instruction to expand the range of the initial medical model, the generation module 210 may expand the range of the initial medical model accordingly. For more information about the user posture, please refer to FIG. 10 and its related description.

In some embodiments, during the operation of the user, the processing module 230 may determine a current viewing window of the user and provide multi-angle side viewing window(s). The current viewing window may show a three-dimensional image that is directly opposite and perpendicular to a viewpoint of the user. A side viewing window may show a three-dimensional image with a different direction than the current viewport. The current viewing window and the side viewing window(s) are used to display the same initial medical model, from different viewpoints. In some embodiments, the current viewing window may be displayed in the three-dimensional space simultaneously with the side viewing window(s), the current viewing window may be located in a center of the field of view of the user, and the side viewing window(s) may be located at an edge of the field of view.

In some embodiments, one or more three-dimensional sub-models included in the initial medical model may be further adjusted during the operation of the user according to a preset adjustment order. A three-dimensional sub-model may refer to a portion of the initial medical model. In some embodiments, the three-dimensional sub-models may be constructed based on the medical imaging data corresponding to the three-dimensional sub-regions in a manner similar to the manner in which the initial medical model is constructed. An exemplary preset adjustment order may refer to adjusting the three-dimensional sub-regions sequentially according to an angle of Z-axis rotation.

In some embodiments, the preset adjustment order may be preset by the system or a user. In some embodiments, the preset adjustment order may be determined based on an order in which the user makes historical adjustments.

In some embodiments, the initial medical model may be pre-stored in a storage device (e.g., the storage device 150), and the processing module 230 may retrieve the initial medical model from the storage device.

In 620, the target medical model may be generated by processing the initial medical model in the three-dimensional space based on the processing instruction(s). In some embodiments, 620 may be performed by the processing module 230.

The target medical model may be a processed three-dimensional medical model, the target medical model may be widely used in modern medical imaging and/or therapeutic fields, and the processing of the initial medical model may be determined based on the subsequent medical treatment corresponding to the target medical model.

In some embodiments, the target medical model may be used for treatment (e.g., to develop a treatment plan). For example, a model processing of the three-dimensional medical model may include determining the contour of a lesion in the target object, and the lesion may refer to a region of the patient to be treated with radiation (e.g., the region where the tumor is located). If radiotherapy is to be performed, a treatment plan (e.g., radiation dose value, dose distribution, etc.) may be set for the lesion region based on the processed three-dimensional medical model (i.e., the target medical model), and an avoidance operation may be performed for the non-lesion region to avoid radiation overload affecting the non-lesion region.

In some embodiments, the target medical model may also be used in the production of training data of the machine learning model. For example, the processing of the three-dimensional medical model may be determined based on an input and output of the machine learning model, with the initial medical model as training input data of the machine learning model and the target medical model as training target data of the machine learning model. Exemplarily, if the machine learning model is used to automatically determine a contour of a three-dimensional medical model of a human body (e.g., a heart model), the input of the machine learning model may be an existing heart model of the human body, and the corresponding target medical model may include a heart model of a specific patient. The processing of the three-dimensional medical model may include determining the contour of the heart of a specific patient, the existing human heart model may be used as training input data/samples and the heart model of the specific patient may be used as training target data/samples.

In some embodiments, the target medical model may also be used for pre-operative planning, medical teaching, treatment process simulation, etc. For example, the target medical model may be used to simulate a surgical or radiotherapy procedure, the model processing may be a simulation of a surgical operation or radiotherapy, and the model operation may include drawing an instruction in which the user may simulate a surgical incision by executing the drawing instruction to determine the surgical operation and procedure for complete removal of the lesion.

The processing of the initial medical model may include at least one operation. Each operation may be accomplished by executing a processing instruction. In some embodiments, a position targeted by the processing operation, i.e., a processing position, may be determined by mapping a user gesture in the three-dimensional space of the initial medical model. For example, the processing position may be a position determined by mapping one or more feature points of a user's hand (e.g., the tip of the user's index finger) in the three-dimensional space of the initial medical model. In some embodiments, the processing position may be a specific position or a specific region of the initial medical model. The specific position may include at least one point of the initial medical model (e.g., a geometric center point, a point on an edge or multiple consecutive points (forming part of a contour line), any point on the initial medical model, etc.). The specific region may correspond to at least a portion of the initial medical model. The specific region may be determined by the user (e.g., selected by the user through a check gesture), set by system default (e.g., one or more regions of a specific tissue, one or more regions of a specific gray scale, etc.), etc. For more information about the user gesture, please refer to FIG. 10 and its related description.

In some embodiments, the initial medical model and the user gesture may be expressed in separate coordinate systems, and the user gesture may be mapped in the three-dimensional space of the initial medical model by fusing a coordinate system of the user gesture with a coordinate system of the initial medical model, to facilitate processing of the initial medical model by the user through the gesture.

In some embodiments, the two coordinate systems may be fused based on a spatial relationship between the coordinate systems of the initial medical model and the user gesture in the three-dimensional space. For example, both coordinate systems may be Cartesian coordinate systems, with the origin of the two coordinate systems being a center point of the initial medical model and a center point of the geometry corresponding to the user gesture, respectively, and the spatial relationship may be described by a vector between the two center points. Exemplarily, the spatial relationship may include a mode of the vector and a direction of the vector. Based on the spatial relationship, the two coordinate systems may be normalized (e.g., the axes are scaled uniformly), and then one of the coordinate systems is fused with the other coordinate system according to a direction and distance shown by the vector.

In some embodiments, the spatial relationship of the coordinate systems may be determined by an operation of the user such as a gesture, a keystroke, a voice, a text instruction, etc. For example, if the initial medical model is presented to the user through VR, AR, and other technologies, the user's hand may be presented to the user's field of view, and the user may move the hand in order to cause the left index finger to touch a special position in the initial medical model, and a displacement vector of the user's hand during this process may serve as the spatial relationship of the coordinate systems.

In some embodiments, the user gesture may be directly set under the same coordinate system when obtaining the user gesture and generating the initial medical model. For example, a coordinate system of a virtual space may be constructed based on a body position of the user, and then the initial medical model may be placed in that virtual space by the user gesture (e.g., dragging, tapping, etc.).

In some embodiments, the initial medical model and the user gesture may have different types of coordinates, and may be converted to the same type of coordinate system and then fused.

For purposes of illustration, the determining of the contour of a lesion (e.g., a specific organ or part thereof) of a target object for radiotherapy is described as an example, which is not intended to limit the scope of the present disclosure. For example, the model processing can be used in the production of training samples of the machine learning model.

In some embodiments, when the user determines the contour of a lesion region of a target object, the user may determine an approximate position of the lesion in the initial medical model from the medical imaging data, and then determine whether the contour of the lesion region has been determined in the initial medical model. If a relevant model of the lesion does not exist in the initial medical model, the user may determine the contour of the lesion at the lesion position according to the morphology of the lesion in the medical imaging data. For example, the user may enter a model drawing mode, process through the user posture to perform a drawing instruction, an erasing instruction, a smoothing instruction, etc., to draw a three-dimensional outline of a lesion model at the lesion position, thus forming a three-dimensional model of the lesion.

If a relevant model of the lesion exists in the initial medical model, the user may adjust the lesion according to the morphology of the lesion in the medical imaging data. For example, the user may enter a model editing mode and adjust the three-dimensional contour of the lesion by the user posture in order to perform model processing instruction(s) such as a dragging instruction, an expansion instruction, a translation instruction, a rotation instruction, etc. After completing the modeling of the lesion, a radiotherapy plan (e.g., radiation duration, radiation dose value, dose distribution, etc.) may be set based on the model of the lesion. Based on the radiotherapy plan, a precise radiotherapy can be performed on the corresponding lesion.

It should be noted that the above description of process 600 is intended to be exemplary and illustrative only, and does not limit the scope of application of the present disclosure. For those skilled in the art, various amendments and changes can be made to process 600 under the guidance of the present disclosure. However, these amendments and changes remain within the scope of the present disclosure. For example, the initial medical model may also be generated by the user by contouring through the user gesture. Exemplarily, the user may enter the model drawing by the user gesture (corresponding to the drawing gesture operation) or by selecting the drawing option in the menu options. During the model drawing, the user may give a drawing instruction, an erasing instruction, and/or a smoothing instruction through one or more user gestures, thereby completing the drawing of the initial medical model. During the model drawing process, the user's hand may use natural movements (such as the user drawing gesture of straightening the index finger and bending the rest of the fingers), and draw according to the contour of the target object or a portion thereof, which reduces the difficulty of editing the initial medical model because the natural movements are closer to the user's regular interaction logic.

Figure 7:
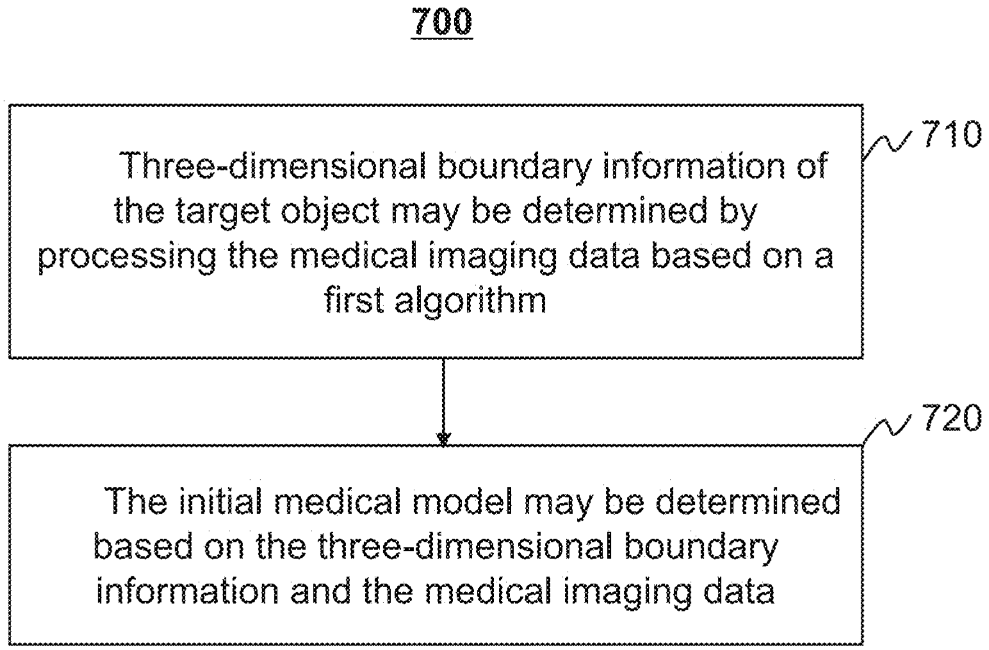
FIG. 7 is a flowchart illustrating an exemplary process for generating an initial medical model according to some embodiments of the present disclosure.

FIG. 7 is a flowchart illustrating an exemplary process for generating an initial medical model according to some embodiments of the present disclosure. In some embodiments, the process 700 may be executed by the system 100 (e.g., the processing device 130) or the system 200 (e.g., the processing module 230). For example, the process 700 may be stored in a storage device (e.g., the storage device 150) in the form of a program or instructions, and the process 700 may be implemented when the processing device 130 or the processing module 230 executes the program or instructions. The schematic diagram of the operation of the process 700 presented below is illustrative. In some embodiments, one or more additional operations not described and/or one or more operations not discussed may be utilized to complete the process. Further, the order of operations of the process 700 illustrated in FIG. 7 and described below is not limiting.

In 710, three-dimensional boundary information of the target object may be determined by processing the medical imaging data based on a first algorithm.

The three-dimensional boundary information may refer to a contour and information related to a boundary of the target object in the three-dimensional space, for example, a position, a shape, a size, etc. In some embodiments, the three-dimensional boundary information may also include information related to boundaries or contours of various portions of the target object. For example, when the target object is the upper body of a patient, the portions of the target object may include bones, lungs, liver, stomach, etc. The three-dimensional boundary information of the target object may include edges or contours of the various portions in the three-dimensional space. For more information about the medical imaging data, please refer to FIG. 3 and its related description.

The first algorithm may be an algorithm or combination of algorithms that can be used to identify edges or contours of various tissues or organs in the image data. For example, the first algorithm may include an edge identification algorithm. An exemplary edge identification algorithm may include a convolution algorithm, in which the image data may be subjected to a convolution operation with a specific operator to determine an edge or contour in the image. The specific operator may include a Roberts operator, a Sobel operator, a Prewitt operator, and a zero-crossing Gaussian operator based on a Laplace operator. In some embodiments, the edge identification algorithm may include visual feature algorithms such as a Canny detector, a boosted edge learning algorithm (BEL). In some embodiments, two-dimensional and/or three-dimensional boundary information of the target object may be determined using the first algorithm.

In some embodiments, if the medical imaging data includes data of multiple two-dimensional medical image sequences, the two-dimensional boundary information of the target object in the various two-dimensional medical images may be determined by the first algorithm, and then the generation of the three-dimensional boundary information may be performed based on a relationship (e.g., a position relationship) between the various two-dimensional medical images and the two-dimensional boundary information. For example, the medical imaging data may include data of multiple CT image sequences (i.e., 2D medical image sequences) of the patient's lungs, wherein a corresponding layer distance of each CT image may be 10 millimeters (mm) with a layer thickness of 10 mm. After determining the two-dimensional edges in the two-dimensional medical images using the first algorithm, the two-dimensional edges may be presented in space according to a scanning order corresponding to the CT image sequences, for example, displaying the two-dimensional edges corresponding to the CT images in space in a top-to-bottom scanning order according to 10 mm layer thickness and 10 mm layer distance of the CT images. Finally, three-dimensional edges may be fitted according to the two-dimensional edges.

In some embodiments, the first algorithm may include an edge identification model, i.e., the three-dimensional boundary information of the target object may be identified based on the edge identification model. The edge identification model may be used to identify the three-dimensional boundary information of the target object based on the medical imaging data of the target object. In some embodiments, the edge identification model is a trained machine learning model. An input of the edge identification model is the medical imaging data of the target object, and an output is the three-dimensional boundary information of the target object. In some embodiments, the edge identification model may be trained based on historical medical imaging data, The training process of the edge identification model may be similar to the training process for determining a model by the display parameter, which is not repeated here.

In 720, the initial medical model may be determined based on the three-dimensional boundary information and the medical imaging data.

In some embodiments, a contour of the initial medical model in the three-dimensional space (also referred to as a three-dimensional contour) may be determined based on the three-dimensional boundary information. In some embodiments, the three-dimensional contour of the initial medical model may be obtained based on a three-dimensional surface reconstruction of the target object based on a boundary contour line extraction algorithm including the Log differential operator. In some embodiments, the three-dimensional contour of the initial medical model may also be determined based on a preset three-dimensional algorithm based on the three-dimensional boundary information. The preset three-dimensional algorithm may be a reconstruction algorithm (e.g., surface masking display, maximum density projection, surface reconstruction, etc.). In some embodiments, the reconstruction algorithm may include, but is not limited to, a Shear-warp algorithm or a Marching Cubes (MC for short) algorithm.

In some embodiments, a preliminary rendering of the initial medical image of the target object may be performed based on the medical imaging data to generate a preliminary rendering model of the target object before determining the three-dimensional boundary information. For example, the preliminary rendered model of the target object may be generated based on a data value in the medical image data (e.g., a CT value in a CT image), and then a boundary, a fill color, a show/hide condition, and other content of the preliminary rendering model may be adjusted based on the three-dimensional boundary information. In some embodiments, the preliminary rendering model may be generated directly based on the medical imaging data, and the contours of the preliminary rendering model or a portion thereof may be filled internally with different grayscales or colors. For example, the grayscale value of each pixel point of the initial medical model may be determined accordingly based on the CT value (in HU as dose unit) of each point of the target object, and the interior of the initial medical model or a portion thereof may be filled based on the grayscale values. As another example, different transparencies and/or colors (e.g., true colors such as green, blue, red, yellow, etc.) may be filled inside the initial medical model or a portion thereof based on a color table. Portions of the initial medical model may be differentiated by filling different transparencies and/or colors in different portions. In some embodiments, the components corresponding to different CT values may be hidden or highlighted according to a Lookup Table (LUT).

Figure 8:
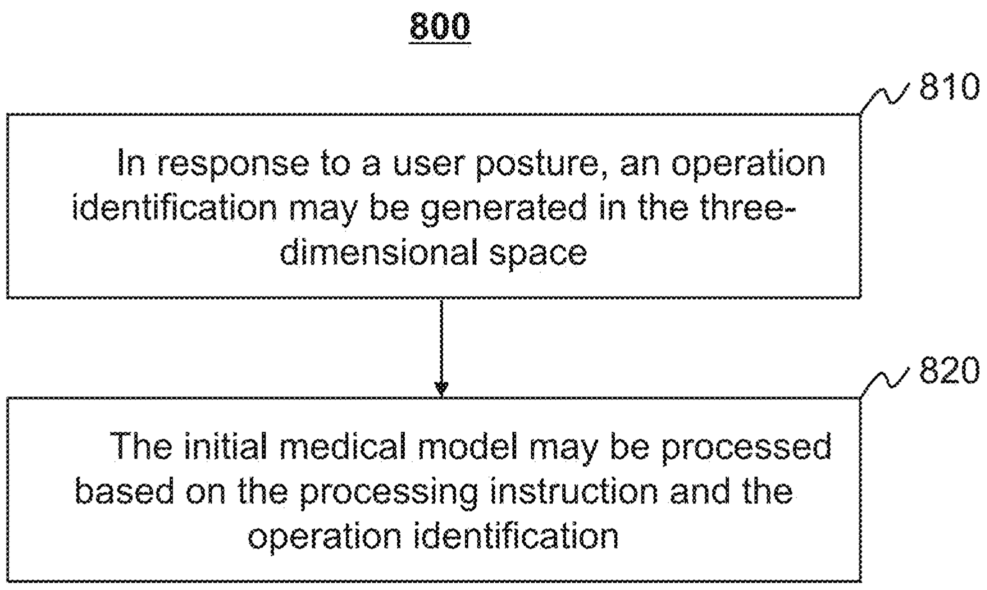
FIG. 8 is a flowchart illustrating an exemplary process for processing an initial medical model according to some embodiments of the present disclosure.

FIG. 8 is a flowchart illustrating an exemplary process for processing an initial medical model according to some embodiments of the present disclosure. In some embodiments, the process 800 may be executed by the system 100 (e.g., the processing device 130) or the system 200 (e.g., the processing module 230). For example, the process 800 may be stored in a storage device (e.g., the storage device 150) in the form of a program or instructions, and the process 800 may be implemented when the processing device 130 or the processing module 230 executes the program or instructions. The schematic diagram of the operation of the process 800 presented below is illustrative. In some embodiments, one or more additional operations not described and/or one or more operations not discussed may be utilized to complete the process. Further, the order of operations of the process 800 illustrated in FIG. 8 and described below is not limiting.

In 810, in response to a user posture, an operation identification may be generated in the three-dimensional space.

To facilitate the operation of the user, an operation identification may be generated in the three-dimensional space where the initial medical model is located. The operation identification may be used to indicate a position of the operation of the user (i.e., a processing position). The position of the operation identification may be a position of the user gesture mapping in the three-dimensional space of the initial medical model. For example, the position of the operation identification may be a position corresponding to the fingertip of the user's index finger. The representation of the operation identification may be set according to actual situations, for example, the operation identification may be represented as a cursor, a specific symbol (e.g., a virtual hand, including a virtual finger, a palm, etc.), etc. In some embodiments, the operation identification may include a virtual hand, and a corresponding gesture operation. At this point the virtual hand may reflect a current user gesture in real time.

In 820, the initial medical model may be processed based on the processing instruction and the operation identification.

In some embodiments, the operation identification may be used to determine a processing position. For example, a point proximate to the operation identification may be determined as a processing position. Exemplarily, in the model drawing or model editing, the processing position may be determined based on the manner described in 920 in FIG. 9, which is not repeated herein.

In some embodiments, the operation identification may include at least two operation sub-identifications. The operation sub-identifications may correspond to the same or different processing instructions. Based on a corresponding processing instruction, each operation sub-identification may be independently controlled for processing, enabling simultaneous execution of multiple processing instructions and improving processing efficiency. For example, the at least two operation sub-identifications may include a first operation sub-identification and a second operation sub-identification. The first operation sub-identification may be used to execute a drawing instruction, and the second operation sub-identification may be used to execute an erasing instruction, a smoothing instruction, etc., to modify a drawing result generated by the first operation sub-identification.

In some embodiments, the first operation sub-identification and the second operation sub-identification may correspond to the left and right hand of the same user or to different fingers of the left and/or right hand of the user, respectively. For example, the first operation sub-identification corresponds to the user's left index finger, and a processing instruction corresponding to the first operation sub-identification may be determined based on a gesture of the user's left index finger; the second operation sub-identification corresponds to the user's left thumb, and a processing instruction corresponding to the second operation sub-identification may be determined based on a gesture of the user's left thumb. In some embodiments, the at least two operation sub-identifications may be separately controlled by different users to achieve online editing, co-editing of the initial medical model.

In some embodiments, the at least two operation sub-identifications may include a primary operation sub-identification and at least one secondary operation sub-identification. If an operation identification for executing a current processing instruction is not specified or cannot be determined, the current processing instruction may be executed via the primary operation sub-identification by default. The user may toggle the primary operation sub-identification and the at least one secondary operation sub-identification to execute the current processing instruction via a specific gesture (e.g., a user-defined gesture or a system default gesture), a menu option, or a shortcut key.

Figure 9:
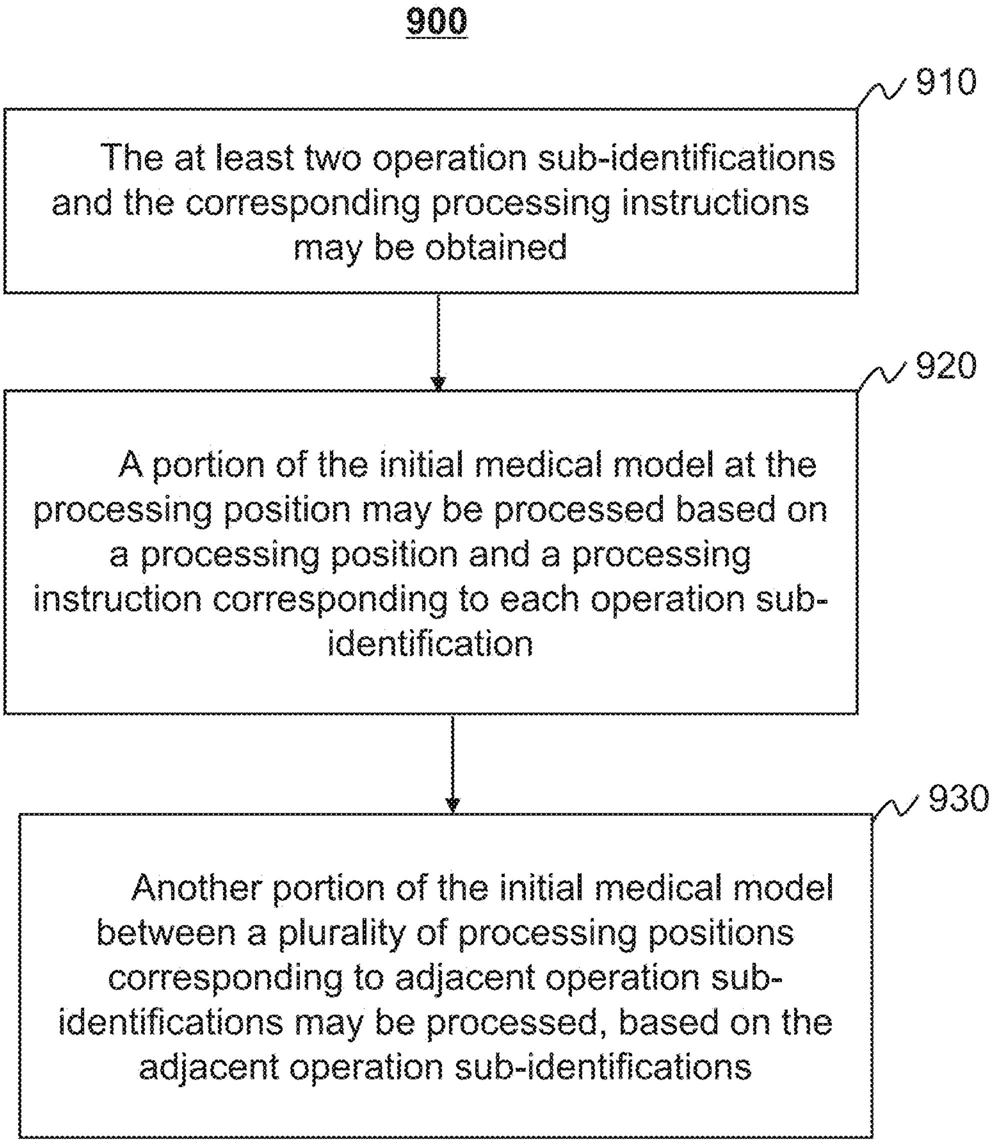
FIG. 9 is a flowchart illustrating an exemplary process for processing an initial medical model based on a plurality of operation sub-identifications according to some embodiments of the present disclosure.

FIG. 9 is a flowchart illustrating an exemplary process for processing an initial medical model based on a plurality of operation sub-identifications according to some embodiments of the present disclosure. In some embodiments, the process 900 may be executed by the system 100 (e.g., the processing device 130) or the system 200 (e.g., the processing module 230). For example, the process 900 may be stored in a storage device (e.g., the storage device 150) in the form of a program or instructions, and the process 900 may be implemented when the processing device 130 or the processing module 230 executes the program or instructions. The schematic diagram of the operation of the process 900 presented below is illustrative. In some embodiments, one or more additional operations not described and/or one or more operations not discussed may be utilized to complete the process. Further, the order of operations of the process 900 illustrated in FIG. 9 and described below is not limiting.

In 910, the at least two operation sub-identifications and the corresponding processing instructions may be obtained.

A number of the at least two operation sub-identifications and/or processing positions may be determined by the user or set by system default. For example, the number of the at least two operation sub-identifications may be two, three, four, five, etc. The at least two operation sub-identifications may be located at different processing positions of the initial medical model. Exemplarily, the at least two operation sub-identifications may include a first operation sub-identification, a second operation sub-identification, and a third operation sub-identification. The first operation sub-identification may be located at a first pending position of the initial medical model, the second operation sub-identification may be located at a second pending position of the initial medical model, and the third operation sub-identification may be located at a third pending position of the initial medical model. In obtaining the number and/or processing positions of the at least two operation sub-identifications, processing instructions corresponding to the operation sub-identifications may be obtained at the same time. Based on the corresponding processing instructions, each operation sub-identification may be independently controlled to execute the corresponding processing instructions to achieve efficient processing.

In some embodiments, the at least two operation sub-identifications may both be cursors. In some embodiments, the at least two sub-identifications may include at least one specific symbol (e.g., a virtual hand).

In some embodiments, the at least two operation sub-identifications may be generated by gestures, menu options, or shortcut keys. For example, a user may open a menu option by making a menu gesture to set the number of the at least two operation sub-identifications.

In 920, a portion of the initial medical model at the processing position may be processed based on a processing position and a processing instruction corresponding to each operation sub-identification.

In some embodiments, a portion of the initial medical model at the processing position may refer to a contour of the initial medical model or a portion thereof at the processing position (also referred to as a contour at the processing position). In some embodiments, the contour at the processing position may be within a certain range of values or sizes. For example, the contour at the processing position is a contour of the initial medical model within a circle with a certain numerical radius centered on a point indicated by an operation sub-identification (e.g., in the form of a cursor). As another example, the medical imaging data of the target object includes multiple medical images, each medical image corresponding to a certain layer thickness. The initial medical model is generated based on the medical imaging data, and the contour at the processing position may be determined based on the layer thickness (e.g., the diameter or equivalent diameter of the contour at the processing position may be the same as the layer thickness). For example, in order to improve the accuracy of the initial medical model modification, the contour at the processing position may be enlarged in an interactive interface by means of an external expansion gesture, where part of the contour of the initial medical model is outside the interactive interface due to the enlargement, and the contour of the initial medical model presented in the interactive interface is determined as the contour at the processing position.

Accordingly, the processing instruction may be to adjust the contour at the corresponding processing position. Through the model drawing and/or model editing, the contour at the processing position may be adjusted so that the target medical model better matches a profile contour of the target object or a portion thereof relative to the initial medical model. For example, through the erasing instruction, the drawing instruction, and the smoothing instruction, an original contour at the processing position may be erased and a new contour may be determined. For example, by using the dragging, expansion, translation, and rotation instructions, the contour at the processing position may be edited/adjusted.

The at least two operation sub-identifications may be controlled independently at the same time (e.g., via the user's left and right hands, respectively, via different fingers of the user's left and/or right hands, or by different users) or sequentially. In some embodiments, it is possible to switch between the two operation sub-identifications described by means of an operation sub-identification switching gesture or a shortcut key. For more information about the processing the initial medical model at each processing position, please refer to the relevant description of 1020 in FIG. 10 of the present disclosure, which is not repeated here.

In 930, another portion of the initial medical model between a plurality of processing positions corresponding to adjacent operation sub-identifications may be processed, based on the adjacent operation sub-identifications.

The adjacent operation sub-identifications refer to operation sub-identifications corresponding to neighboring processing positions. The portion of the initial medical model between the multiple processing positions corresponding to the adjacent operation sub-identifications is an unprocessed portion of the initial medical model. For example, the medical imaging data of the target object includes data of 20 medical images, each medical image corresponding to a certain layer thickness. The initial medical model is generated based on the medical imaging data. Accordingly, the initial medical model may be divided into 20 layers, each layer corresponding to one medical image. When a portion of the contour of the initial medical model in layers 5, 7 and 10 is processed (e.g., erasing the original contour, drawing a new contour, or adjusting the original contour by dragging, scaling, translating, rotating, etc.) by the operation sub-identifications, the unprocessed contour may include a portion of the contour in layers 6, 8 and 9.

In some embodiments, the processing of a portion of the initial medical model between a plurality of processing positions corresponding to adjacent operation sub-identifications may include processing an unprocessed portion of the initial medical model between the processing positions based on an operation at the processing positions corresponding to the at least two operation sub-identifications. In the example of contour processing described above, the processing of the unprocessed portion of the initial medical model between the processing positions includes smoothing the unprocessed contour. Exemplarily, when the user processes the partial contours of layers 5, 7, and 10 by manipulating the operation sub-identifications, a portion of the contours of layers 6, 8, and 9 may be smoothed based on the original contour and the modified contours of layers 5, 7, and 10. In some embodiments, the smoothing may be determined by an interpolation algorithm. For example, a contour adjustment magnitude of the layer corresponding to the at least two operation sub-identifications may be determined based on the at least two operation sub-identifications and the corresponding processing instructions, and then an interpolation operation may be performed based on the adjustment magnitude to obtain a contour adjustment magnitude of the portion between the layers corresponding to the at least two operation sub-identifications.

Figure 10:
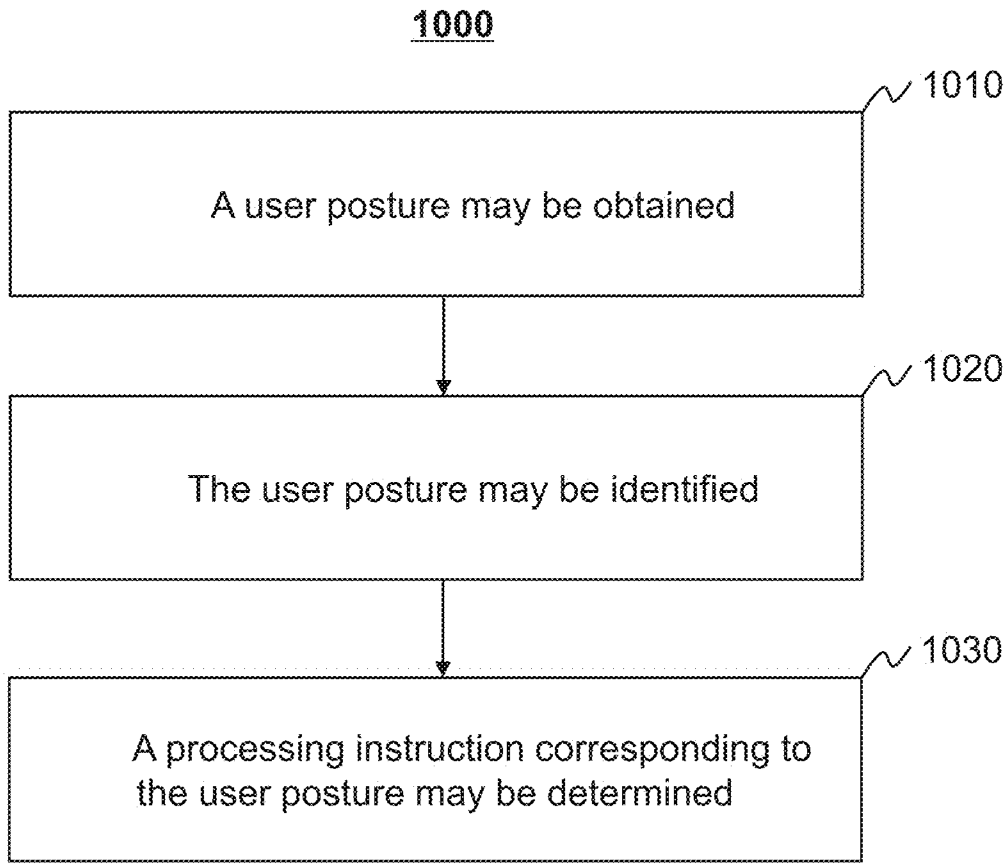
FIG. 10 is a flowchart illustrating an exemplary process for obtaining one or more processing instructions of a user according to some embodiments of the present disclosure.

FIG. 10 is a flowchart illustrating an exemplary process for obtaining one or more processing instructions of a user according to some embodiments of the present disclosure. In some embodiments, process 1000 may be executed by the system 100 (e.g., the processing device 130) or the system 200 (e.g., the instruction determination module 220). For example, the process 1000 may be stored in a storage device (e.g., the storage device 150) in the form of a program or instructions, and the process 1000 may be implemented when the processing device 130 or the instruction determination module 220 executes the program or instructions. The schematic diagram of the operation of the process 1000 presented below is illustrative. In some embodiments, one or more additional operations not described and/or one or more operations not discussed may be utilized to complete the process. Further, the order of operations of the process 1000 illustrated in FIG. 10 and described below is not limiting.

In 1010, a user posture may be obtained.

The user posture refers to a form and/or movement of the user's entire body or a portion of a limb. The portion of the limb may include the user's hands (e.g., fingers, knuckles, palms, wrists, etc.), extremities (e.g., arms, legs, etc.), or combinations thereof. For example, the user posture may include the form or movement of the user's fingers, such as the index finger being straight, the remaining fingers other than the index finger being bent, etc. As another example, the user posture may include the form or movement of the user's arms, such as arms raised, arms naturally hanging down, arms waving, etc.

In some embodiments, the user posture may be determined by a position and movement of a feature point in space. The feature point may refer to a part of the user's body that reflects the form and/or movement of the user's whole body or a portion of the limb. For example, the feature point may be a user's body joint point (e.g., knee, elbow, wrist, etc.), a vital organ (e.g., lung, head, etc.), a limb (e.g., hand, including fingers, knuckles, fingertips, palm, etc.), etc.; or other key points of the user, such as a body center of gravity, a hand center of gravity point, a body center point, a hand center point, etc.

For the purpose of illustration, this embodiment specifies the relevant content of the method for obtaining and determining the user's posture, taking the user's hand form and movement (i.e., gesture) as an example. The relevant description of the user's gesture in the present disclosure can be applied to other specific postures (e.g., the user's arm posture, etc.).

The user gesture may refer to a hand form and/or movement of the user. In some embodiments, the user gesture may include real-time position information of one or more feature points of the hand, as well as motion information. The real-time position information may refer to a real-time position of one or more feature points (e.g., individual fingers, fingertips, etc.) in a three-dimensional spatial coordinate system. The real-time position information may be in the form of coordinates, angles, etc. The motion information may refer to a motion of one or more feature points, e.g., motion trajectory, motion trend, etc. For example, the motion information may include a change in the user's left index finger from straight to curved. In some embodiments, the motion information may be determined based on the real-time position of a specific portion of the user's hand at one or more moments (e.g., 10 seconds, 30 seconds, 1 minute, 2 minutes, etc.).

In some embodiments, the instruction determination module 220 may obtain limb depth information corresponding to the user posture based on a posture identification device; and determine the user posture based on the limb depth information.

The posture identification device is a device for obtaining the user posture. The posture identification device may include a gesture detector, a camera, a sensor device, etc.

The limb depth information may reflect position information of a specific body part of the user in the three-dimensional space. The form of the limb depth information is related to the actual needs and the way the limb depth information is collected. For example, the limb depth information may be coordinates of various feature points of a specific body part of the user under a spatial coordinate system. As another example, the limb depth information may be point cloud data in space for a specific body part of the user (e.g., a hand).

In some embodiments, if the user posture includes a user gesture, the depth information corresponding to the user gesture may be obtained by a gesture detector. The gesture detector may refer to a sensor or a combination of sensors for detecting a user gesture, for example, the gesture detector may include at least one of a camera, a depth camera, a sensing glove, an ultrasonic sensor, an inertial sensor, and other sensors.

In some embodiments, the instruction determination module 220 may determine the user posture based on the limb depth information. For example, the current limb depth information may be searched in a preset comparison table to determine reference limb depth information that is similar to the current limb depth information, and a reference user posture corresponding to the reference limb depth information is determined as the user posture corresponding to the current limb depth information. The preset comparison table may include a correspondence between different reference limb depth information and reference user postures. The preset comparison table may be obtained by constructing the correspondence between the reference limb depth information and the reference user postures based on a priori knowledge or historical data.

In 1020, the user posture may be identified. In 1030, a processing instruction corresponding to the user posture may be determined.

In some embodiments, the instruction determination module 220 may identify a user posture in a variety of ways. For example, by comparing a current user posture to a posture database, a reference posture that matches the current user posture may be determined, and a processing instruction corresponding to the reference posture may be determined as the processing instruction corresponding to the current user posture.

In some embodiments, the instruction determination module 220 may determine a target posture operation based on an identification result of the user posture; and determine a processing instruction corresponding to the target posture operation based on a correspondence between posture operations and processing instructions.

As mentioned above, the present disclosure specifies the process for identifying a user posture, using the user gesture and the gesture operation (corresponding to the posture operation) as an example. The relevant description of the user gesture in the present disclosure can be applied to other specific postures (e.g., the user's arm posture, etc.).

In some embodiments, a target gesture operation corresponding to the user gesture is determined by comparing the obtained user gesture to at least one gesture operation in a preset set of gesture operations. The gesture operation may refer to a specific gesture that is normalized or customized. For example, the gesture operation may include a tap of a certain finger, a pinch of a finger, a slide of a finger or palm, a rotation, etc. In some embodiments, at least one gesture operation in the set of gesture operations may be preset by the user. For example, a specific gesture of the user is obtained by a gesture detector and that specific gesture is defined as a gesture operation in the set of gesture operations. In some embodiments, the at least one gesture operation may be determined by other input devices (e.g., via a mouse, keyboard, etc.) in a textual description or pictorial manner.

In some embodiments, the identification of the user gesture may be achieved by a similarity algorithm. In some embodiments, a specific vector or group of vectors corresponding to the user gesture may be determined based on a feature point of the user gesture. Exemplarily, a specific vector between a feature point of the user's hand (e.g., the fingertips, knuckles, and center of the palm of each finger) may be generated based on a coordinate of the feature point of the user's hand. For example, a thumb vector for describing the morphology and movement of the thumb may be generated based on the thumb tip, the middle knuckle point, and the palm center point. For example, the specific vectors corresponding to each finger of the left and right hands may be generated with reference to the method for determining the thumb vector to determine the left hand vector group and the right hand vector group. Then, the similarity of the specific vector or the group of vectors to the vectors or the group of vectors corresponding to the various gesture operations in the set of gesture operations is calculated. Exemplarily, the left and right hand vector groups corresponding to the preset gesture operations in the set of gesture operations may be compared with the left and right hand vector groups of the current user gesture, the similarity of which may be determined based on a distance between the various corresponding feature points (e.g., the similarity may be the inverse of the geometric mean of the feature point distances). The gesture operations corresponding to the vector groups whose similarity is higher than a threshold may be selected as the target gesture operations. The threshold may be preset as described, for example, 0.6, 0.7, 0.8, 0.9, etc., depending on the actual situations. Exemplarily, the similarity algorithm may include a cosine similarity algorithm, a Euclidean distance, and other vectorial similarity calculation methods.

In some embodiments, the target gesture operation may also be identified based on a gesture identification model. The gesture identification model is used to identify a target gesture operation based on a user gesture. In some embodiments, the gesture identification model is a trained machine learning model. An input of the gesture recognition model is a user gesture, and an output of the gesture recognition model is a target gesture operation corresponding to the user gesture. Exemplary machine learning models may include a neural network model (e.g., a deep learning model), a generative adversarial network (GAN), a deep confidence network (DBN), a stacked autoencoder (SAE), a logistic regression (LR) model, a support vector machine (SVM) model, a decision tree model, a plain Bayesian model, a random forest model, or a restricted Boltzmann machine (RBM), a gradient Boosted Decision Tree (GBDT) model, a Lambda MART model, an adaptive augmentation model, a Hidden Markov model, a perceptron neural network model, a Hopfield network model, etc., or any combination thereof. Exemplary deep learning models may include a deep neural network (DNN) model, a convolutional neural network (CNN) model, a recurrent neural network (RNN) model, a feature pyramidal network (FPN) model, etc. Exemplary CNN models may include a V-Net model, a U-Net model, a FB-Net model, a Link-Net model, etc., or any combination thereof.

In some embodiments, the gesture identification model is obtained by training using historical user gestures and corresponding historical target gesture operations as sample pairs. Specifically, the historical user gestures are used as the training inputs and the historical target gesture operations are used as the training targets. The historical user gestures are user gestures set by the user or entered during the previous gesture identification process. The historical target gesture operations may be target gesture operations corresponding to the historical user gestures, and the historical gesture operations may be manually labeled by the user or determined based on historical identification results. In the training process, samples may be input into the gesture identification model, and the model output results and the sample labels are input into a loss function, and relevant parameters in the model are updated based on a loss function result of the model, and when the loss function result meets an output criterion, an updated gesture identification model may be used as the trained gesture identification model.

In some embodiments, there may be a one-to-one correspondence between the gesture operation and the processing instruction. After determining the target gesture operation, a corresponding processing instruction of the target gesture operation may be determined based on its correspondence.

Because there are a limited number of actions consistent with human habits, there is not an exclusive reliance on gesture operations. In other embodiments, the same gesture operation, in different processing modes, may correspond to different processing instructions. The instruction determination module 220 may obtain the current processing mode and determine specific processing instructions based on the current processing mode. For example, for the gesture operation of palm rotation, the gesture operation may correspond to the processing instruction of rotating a selected portion of the initial medical model during model editing, and the gesture operation may correspond to the processing instruction of rotating the perspective during perspective adjustment.

In some embodiments, the current processing mode may be determined at least based on auxiliary information (e.g., mouse, keystroke, voice, body movement, etc.). For example, the processing mode may be embodied as an option menu of multiple processing modes, with the option menu including an option table from which the current processing mode is selected via the auxiliary information. In some embodiments, the option menu may be opened by the user making a menu gesture. As another example, the user selects the desired processing type directly by pressing a shortcut key on the keyboard. Each shortcut key corresponds to one processing mode.

In some embodiments, the processing mode of the initial medical model may include one or more processing modes such as a regular operation mode, a perspective adjustment mode, a model editing mode, a model drawing mode, a value adjustment mode, etc. The processing modes may include at least one processing operation.

The regular operation mode refers to a generalized editing of the three-dimensional model. In some embodiments, the regular operation mode does not require the aid of the auxiliary information, and the processing instructions in the regular operation mode may be generalized in other modes. The regular operation mode may include a check instruction and a menu instruction. The check instruction may be determined by a check gesture operation (e.g., a tap of the left index finger), and the corresponding processing instruction may be to check a portion of the model at the current processing position, and the selected portion of the model may be used as the execution object for subsequent processing operations, e.g., the initial medical model contains a lesion to be adjusted, and the selection of the lesion may be achieved by a tap operation of the left index finger. The menu instruction may be determined by a menu gesture operation (e.g., a long press of the left index finger), and the corresponding processing instruction may be to pop up a menu option at the current processing position and select the option in the menu by a check gesture operation. Exemplarily, the menu option may include, for example, an edit option and an edit tool option, and when the user selects the edit option, the model processing enters model editing; if one of the edit tools is selected, the processing instruction corresponding to the edit tool may be executed. For example, the edit tool may include showing/hiding a model, and if the edit tool is selected, the tool may control the show or hide of the currently selected portion of the model.

In the perspective adjustment mode, a viewing angle of the initial medical model may be adjusted. In some embodiments, perspective adjustment is performed when the user checks a perspective control option in the menu options. The perspective adjustment may include a rotation instruction, a displacement instruction, a scaling instruction, and a reset instruction. The rotation instruction may be determined by a rotation gesture operation (e.g., flip of the left hand palm), and the corresponding processing instruction may be to synchronously rotate the selected object in a specific plane according to the motion trajectory of the rotation gesture operation (e.g., treating the hand as an object in the screen and rotating the object in the screen along with the angle of hand rotation when the user rotates the hand). The displacement instruction may be determined by a displacement gesture (e.g., five fingers straightened and moved), and the corresponding processing instruction may be to move the selected object synchronously in a two-dimensional plane according to the motion trajectory of the displacement gesture. The scaling instruction may be determined by a scaling gesture (e.g., moving the right palm back and forth), and the corresponding processing instruction may be to adjust the size of the object (equivalent to adjusting the distance of the object) according to the specific position of the gesture, e.g., pushing the palm forward to shrink and pulling back to enlarge. The reset instruction may be determined by resetting the gesture operation (e.g., five-finger pinch), and the corresponding processing instruction may be to reset the current view of the screen.

In the model editing mode, the initial medical model or its components (e.g., its contour) may be edited/adjusted (e.g., dragged, scaled, translated, rotated, etc.). In some embodiments, the model editing is entered when the user selects an edit option in the menu options. The model editing may include a dragging instruction, an expansion instruction, a translation instruction, and/or a rotation instruction. The dragging instruction may be to drag the selected point according to a motion trajectory of a dragging gesture operation. The expansion instruction stretches and pushes the selected contour outward and inward according to a trajectory of an expansion gesture operation. The translation instruction may be to translate the selected contour according to a motion trajectory of a translation gesture operation. The rotation instruction may be to rotate the selected contour on an axis of the center of the contour according to a motion trajectory of a rotation gesture operation. In some embodiments, different instructions (e.g., dragging instruction, expansion instruction, translation instruction, rotation instruction) may be determined by options in the menu. In some embodiments, different instructions may be determined by different gesture operations. By way of example only, the dragging instruction may be determined by a gesture operation in which the fingers are pinched together and moved, the expansion instruction may be determined by a gesture operation in which the five fingers are straightened and moved, and the translation instruction may be determined by a gesture operation in which the hand is moved. The rotation command may be determined by a gesture operation with the right hand palm flipped. The angle of rotation is the same as or proportional to the angle of palm flip.

In the model drawing mode, a contour of a three-dimensional shape may be determined, for example, by erasing an original contour, determining a new contour, etc. In some embodiments, the model drawing is entered when the user selects a draw option in the menu options. The model drawing may include a drawing instruction, an erasing instruction, and a smoothing instruction. The drawing instruction may be determined by a drawing gesture (e.g., right index finger straightened and moved), and the corresponding processing instruction may be to generate a corresponding drawing image at the processing position according to a motion trajectory of a drawing gesture operation. The erasing instruction may be determined by an erasing gesture (e.g., right index and middle finger straightened and moved), and the corresponding processing instruction may be to erase the corresponding drawing image at the processing position according to a motion trajectory of an erasing gesture operation. The smoothing instruction may be determined by a smoothing gesture (e.g., right hand with five fingers straight and together), and the corresponding processing instruction may be to smooth the drawing image at the processing position based on a motion trajectory of a smoothing gesture operation.

The value adjustment mode may be used to make adjustments to at least a portion of the parameters of the initial medical model. In some embodiments, the user may adjust the corresponding data by a specific shortcut key. For example, the transparency of the currently selected object is increased when the transparency plus shortcut key is pressed, and the transparency of the currently selected object is decreased when the transparency minus shortcut key is pressed. In some embodiments, the user may adjust the corresponding data by a specific value adjustment gesture operation. For example, the user may indicate the corresponding data by a distance between the thumb and the index finger, with a minimum value (e.g., 0) indicated when the thumb is fully pinched to the index finger and a maximum value indicated when the thumb is at 90° to the index finger. In some embodiments, the corresponding data may be adjusted by combining the specific shortcut key with the value adjustment gesture operation. Exemplarily, to improve the accuracy of the input values, the gesture operation may be combined with the shortcut key during data input, and when the shortcut key is pressed, a relative position of a processing position to a center of the screen may be obtained, and a unit-by-unit increase or decrease of the value may be achieved by adjusting the processing position relative to the center of the screen by a user gesture. When the shortcut key is pressed again, the value adjustment ends. In some embodiments, when the user adjusts a value, an initial value adjustment may be made by gesture adjustment, and then a unit-by-unit precise adjustment may be made by a keystroke or a combination of keystroke and gesture operation.

Embodiments of the present disclosure further provide non-transitory computer-readable storage medium, comprising a set of instructions, wherein when executed by a processor, the aforementioned method for processing a three-dimensional model is implemented.

Embodiments of the present disclosure have at least the following beneficial effects.

(1) By directly displaying the three-dimensional medical image of the target object in the three-dimensional space, radiotherapists can directly browse and modify the data in the three-dimensional space based on the operation consistent with human habits, thus improving the convenience of interaction and work efficiency. At the same time, by determining the display parameters of different voxels or tissues in the medical imaging data, different colors and transparencies can be used to visualize and highlight different voxels or tissues for the radiotherapists to observe them intuitively.

(2) By displaying both the three-dimensional medical image and a certain cross-sectional image in the three-dimensional space, a structure, a position, and a size of the lesion region can be visually reflected, which is easy for the radiotherapist to observe. At the same time, displaying a certain layer of cross-sectional images can facilitate better observation of lossless texture information as well as to take advantage of the radiotherapist's past experience in processing on a two-dimensional plane.

(3) By identifying and displaying the two-dimensional rendered image in the three-dimensional space, it can facilitate the radiotherapist to process the lesion region of the target object in conjunction with the past experience of processing in the two-dimensional plane.

(4) The present disclosure identifies the processing instruction of the initial medical model by the user gesture and processes the initial medical model, realizing the three-dimensional processing of the initial medical model based on gestures, which is more intuitive to observe the contour of the region in the three-dimensional case without frequently switching pages than the two-dimensional operation and is more in line with human intuition. Specifically, when processing, the three-dimensional model is processed directly without adjusting image data of the initial medical model one by one, which improves the efficiency of the relevant practitioners.

(5) The present disclosure introduces a gesture operation and a natural action, which is closer to the user's regular interaction logic and reduces the difficulty of editing the initial medical model.

(6) The present disclosure allows contouring by multiple identifications by increasing the number of operation identifications: each identification can be controlled independently, which can improve the hand identification accuracy and control and adjust the three-dimensional model more precisely. In addition, it allows the pulling process of the contours to be more flat, and the model between various identifications can be determined by fitting, which in turn makes the contour modification results closer to expectations.

The basic concepts have been described above, apparently, in detail, as will be described above, and does not constitute limitations of the disclosure. Although there is no clear explanation here, those skilled in the art may make various modifications, improvements, and modifications of present disclosure. This type of modification, improvement, and corrections are recommended in present disclosure, so the modification, improvement, and the amendment remain in the spirit and scope of the exemplary embodiment of the present disclosure.

What is claimed is:

1. A method implemented on at least one machine each of which has at least one processor and at least one storage device for image processing, comprising:

generating a three-dimensional medical image of a target object based on medical imaging data of the target object, and displaying the three-dimensional medical image on a laptop or a desktop computer, the three-dimensional medical image including an initial medical model of the target object;

obtaining one or more processing instructions of a user, including;

obtaining a user posture based on a posture identification device, the user posture being expressed in a real three-dimensional space;

identifying the user posture; and determining the one or more processing instructions corresponding to the user posture, wherein the one or more processing instructions include an instruction to perform a contouring operation on the three-dimensional medical image; and generating, in response to the user posture, an operation identification in the laptop or the desktop computer, wherein a position of the operation identification is a position of a user posture in the real three-dimensional space mapping in a three-dimensional space of the initial medical model in the laptop or the desktop computer, and the operation identification includes a cursor or a specific symbol for simulating the user posture and movements in the three-dimensional space to execute the contouring operation;

generating a target medical model by contouring the initial medical model under an indication of the operation identification, in the laptop or the desktop computer, based on the one or more processing instructions, the target medical model including a contour of a region of interest (ROI) and/or a contour of a point of interest (POI).

2. The method of claim 1, wherein the target medical model further includes two-dimensional contour information, and the generating a target medical model includes:

determining a first datum plane in the three-dimensional medical image;

generating the two-dimensional contour information in the first datum plane based on the one or more processing instructions; and displaying the target medical model obtained by contouring the three-dimensional medical image and the two-dimensional contour information obtained by contouring a cross-sectional image in the laptop or the desktop computer at the same time.

3. The method of claim 1, wherein the three-dimensional medical image is generated by:

determining a display parameter of at least one tissue in the three-dimensional medical image based on a tissue type and/or a spatial position relationship between different tissues in the medical imaging data.

4. The method of claim 3, wherein the determining a display parameter of at least one tissue in the three-dimensional rendered image based on a tissue type and/or a spatial position relationship between different tissues in the medical imaging data includes:

determining the display parameter of the at least one tissue in the three-dimensional rendered image by a first preset rule based on the tissue type and/or the spatial position relationship between the different tissues in the medical imaging data, wherein the first preset rule includes that an Alpha value in the display parameter of a target tissue among the at least one tissue is set to be lower than a first threshold and an Alpha value in the display parameter of a tissue related to the target tissue is set to be higher than a second threshold, and/or the first preset rule includes that an RGB value in the display parameter of the target tissue is set to be different from an RGB value in the display parameter of the tissue related to the target tissue.

5. The method of claim 3, wherein the determining a display parameter of at least one tissue in the three-dimensional rendered image based on a tissue type and/or a spatial position relationship between different tissues in the medical imaging data includes:

determining the display parameter of the at least one tissue in the three-dimensional rendered image by a display parameter determination model based on the tissue type and/or the spatial position relationship between the different tissues in the medical imaging data, wherein the display parameter determination model is a machine learning model.

6. The method of claim 3, wherein the medical imaging data includes a three-dimensional body data set of the target object, the determining a display parameter of at least one tissue in the three-dimensional rendered image based on a tissue type and/or a spatial position relationship between different tissues in the medical imaging data includes:

determining the display parameter of the at least one tissue in the three-dimensional rendered image by a second preset rule based on the tissue type and/or the spatial position relationship between the different tissues in the medical imaging data, wherein the second preset rule includes that the display parameter of the at least one tissue in the three-dimensional rendered image are determined based on a value domain and a spatial domain of the medical imaging data.

7. The method of claim 1, wherein the method further includes:

determining, based on the medical imaging data, a target region, wherein the target region is a tumor target region (GTV) of the target object; and generating an initial medical model based on a preset processing range and the target region, wherein generating the initial medical model based on a preset processing range and the target region includes:

dividing the target region into multiple three-dimensional sub-regions;

determining a processing sub-region of each three-dimensional sub-region based on a range determination model;

obtaining the preset processing range by fusing multiple processing sub-regions; and generating the initial medical model by expanding a three-dimensional shape of the target region based on the preset processing range, wherein the three-dimensional medical image is generated based on the initial medical model.

8. The method of claim 1, wherein the operation identification includes at least two operation sub-identifications, the generating a target medical model by contouring the initial medical model under an indication of the operation identification, in the laptop or the desktop computer, based on the one or more processing instructions includes:

for each operation sub-identification of the at least two operation sub-identifications, processing the initial medical model in the laptop or the desktop computer based on the each operation sub-identification and a corresponding processing instruction of the one or more processing instructions.

9. The method of claim 8, wherein the each operation sub-identification corresponds to two or more processing positions, the generating a target medical model by contouring the initial medical model under an indication of the operation identification, in the laptop or the desktop computer, based on the one or more processing instructions includes:

processing a portion of the initial medical model in the laptop or the desktop computer at a processing position, of the two or more processing positions, corresponding to the each operation sub-identification based on the processing position and a processing instruction, of the one or more processing instructions, corresponding to the each operation sub-identification; and processing another portion of the initial medical model in the laptop or the desktop computer between a plurality of processing positions, of the two or more processing positions, corresponding to adjacent operation sub-identifications of the at least two operation sub-identifications, based on the adjacent operation sub-identifications.

10. The method of claim 9, wherein a processing mode of the initial medical model in the three-dimensional space includes at least one of: a general operation mode, a viewpoint adjustment mode, a model editing mode, a model drawing mode, or a numerical adjustment mode.

11. The method of claim 1, wherein the obtaining the user posture includes:

obtaining, based on a posture identification device, limb depth information corresponding to the user posture; and determining the user posture based on the limb depth information.

12. The method of claim 1, wherein the determining the one or more processing instructions corresponding to the user posture includes:

determining, based on an identification result of the user posture, a target posture operation; and determining, based on a correspondence between posture operations and processing instructions, the one or more processing instructions corresponding to the target posture operation.

13. The method of claim 1, wherein the method further includes:

mapping the user posture in the three-dimensional space of the initial medical model in the three-dimensional space by fusing a coordinate system of the user posture with a coordinate system of the initial medical model in the three-dimensional space.

14. The method of claim 1, wherein the method further includes:

determining a current viewing window of the user and provide multi-angle side viewing windows during the contouring operation of the user, wherein the current viewing window shows the three-dimensional image that is directly opposite and perpendicular to a viewpoint of the user, the multi-angle side viewing windows show the three-dimensional image with a different direction than the current viewing window, and the current viewing window and the multi-angle side viewing windows are used to display the initial medical model in a three-dimensional space from different viewpoints.

15. The method of claim 14, wherein when the current viewing window is displayed in the three-dimensional space simultaneously with the multi-angle side viewing windows, the current viewing window is located in a center of a field of view of the user, and the multi-angle side viewing windows are located at an edge of the field of view.

16. The method of claim 1, wherein a same gesture operation, in different processing modes, corresponds to different processing instructions.

17. The method of claim 1, wherein the method further includes:

determining a second datum plane based on the medical imaging data;

generating, based on the medical imaging data and the second datum plane, a two-dimensional rendered image of the target object; and displaying the two-dimensional rendered image in the three-dimensional space.

18. A system for processing a three-dimensional image, comprising:

at least one storage device storing a set of instructions; and at least one processor in communication with the storage device, wherein when executing the set of instructions, the at least one processor is configured to cause the system to perform operations including:

generating a three-dimensional medical image of a target object based on medical imaging data of the target object, and displaying the three-dimensional medical image on a laptop or a desktop computer, the three-dimensional medical image including an initial medical model of the target object;

obtaining one or more processing instructions of a user, including:

obtaining a user posture based on a posture identification device. the user posture being expressed in a real three-dimensional space;

identifying the user posture;

determining the one or more processing instructions corresponding to the user posture, wherein the one or more processing instructions include an instruction to perform a contouring operation on the three-dimensional medical image; and generating, in response to the user posture, an operation identification in the laptop or the desktop computer, wherein a position of the operation identification is a position of a user posture in the laptop or the desktop mapping in the three-dimensional space of the initial medical model in the laptop or the desktop computer, and the operation identification includes a cursor or a specific symbol for simulating the user posture and movements in the three-dimensional space to execute the contouring operation;

generating a target medical model by contouring the initial medical model under an indication of the operation identification. in the laptop or the desktop computer, based on the one or more processing instructions, the target medical model including a contour of a region of interest (ROI) and/or a contour of a point of interest (POI).

19. A non-transitory computer readable medium storing instructions, the instructions, when executed by at least one processor, causing the at least one processor to implement a method comprising:

generating a three-dimensional medical image of a target object based on medical imaging data of the target object, and displaying the three-dimensional medical image in a laptop or a desktop computer, the three-dimensional medical image including an initial medical model of the target object obtaining one or more processing instructions of a user, including:

obtaining a user posture based on a posture identification device, the user posture being expressed in a real three-dimensional space;

identifying the user posture;

determining the one or more processing instructions corresponding to the user posture, wherein the one or more processing instructions include an instruction to perform a contouring operation on the three-dimensional medical image; and generating, in response to the user posture, an operation identification in the laptop or the desktop computer, wherein a position of the operation identification is a position of a user posture in the laptop or the desktop mapping in the three-dimensional space of the initial medical model in the laptop or the desktop computer, and the operation identification includes a cursor or a specific symbol for simulating the user posture and movements in the three-dimensional space to execute the contouring operation;

generating a target medical model by contouring the initial medical model under an indication of the operation identification, in the laptop or the desktop computer, based on the one or more processing instructions, the target medical model including a contour of a region of interest (ROI) and/or a contour of a point of interest (POI).

* * * * *